United States Patent
Inghardt et al.

(10) Patent No.: US 6,750,243 B1
(45) Date of Patent: Jun. 15, 2004

(54) AMIDINO DERIVATIVES AND THEIR USE AS THROMBIN INHIBITORS

(75) Inventors: Tord Inghardt, Frillesás (SE); Olle Karlsson, Mölndal (SE); Marcel Linschoten, Västra Frölunda (SE); Jan-Erik Nyström, Rönninge (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/509,032

(22) PCT Filed: Dec. 10, 1999

(86) PCT No.: PCT/SE99/02316

§ 371 (c)(1),
(2), (4) Date: Mar. 21, 2000

(87) PCT Pub. No.: WO00/35869

PCT Pub. Date: Jun. 22, 2000

(30) Foreign Application Priority Data

Dec. 14, 1998 (SE) ................................................ 9804313

(51) Int. Cl.$^7$ .................. A61K 31/4025; C07D 405/02
(52) U.S. Cl. .................. 514/422; 548/525; 548/953
(58) Field of Search .................. 548/525, 953; 514/422

(56) References Cited

U.S. PATENT DOCUMENTS

| 4,346,078 A | 8/1982 | Bajusz et al. |
| 5,705,487 A | 1/1998 | Schacht et al. |
| 5,707,966 A | 1/1998 | Schacht et al. |
| 5,710,130 A | 1/1998 | Schacht et al. |
| 5,744,487 A | 4/1998 | Ohshima et al. |

FOREIGN PATENT DOCUMENTS

| EP | 0 185 390 | 6/1986 |
| EP | 0 195 212 A2 | 9/1986 |
| EP | 0 293 881 | 12/1988 |
| EP | 0 362 002 A1 | 4/1990 |
| EP | 0 364 344 | 4/1990 |
| EP | 0 468 231 A2 | 1/1992 |
| EP | 0 468 231 A3 | 1/1992 |
| EP | 0 526 877 A3 | 2/1993 |
| EP | 0 526 877 A2 | 2/1993 |
| EP | 0 530 167 A | 3/1993 |
| EP | 0 542 525 A2 | 5/1993 |
| EP | 0 559 046 | 9/1993 |
| EP | 0 601 459 | 6/1994 |
| EP | 0 623 596 | 11/1994 |
| EP | 0 641 779 A1 | 3/1995 |
| EP | 0 648 780 A1 | 4/1995 |
| EP | 0 669 317 A1 | 8/1995 |
| EP | 0 672 658 | 9/1995 |
| EP | 0 686 642 | 12/1995 |
| WO | 97/46577 | 12/1977 |
| WO | 93/11152 | 6/1993 |
| WO | 93/18060 | 9/1993 |
| WO | 94/29336 | 12/1994 |
| WO | 95/23609 | 8/1995 |
| WO | 95/35309 | 12/1995 |
| WO | 96/03374 | 2/1996 |
| WO | 96/25426 | 8/1996 |
| WO | 96/31504 | 10/1996 |
| WO | 96/32110 | 10/1996 |
| WO | 97/02284 | 1/1997 |
| WO | 97/23499 | 7/1997 |
| WO | 97/49404 | 12/1997 |
| WO | 98/06740 | 2/1998 |
| WO | 98/57932 | 12/1998 |

*Primary Examiner*—Joseph K. McKane
*Assistant Examiner*—Kamal Saeed
(74) *Attorney, Agent, or Firm*—Nixon & Vanderhye

(57) ABSTRACT

There is provided compounds of formula I

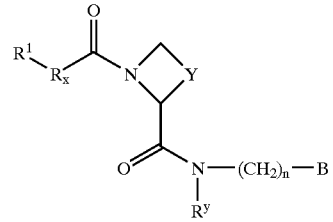

wherein $R^1$, $R_x$, Y, $R^y$, n and B have meanings given in the description which are useful as competitive inhibitors of trypsin-like proteases, such as thrombin, and in particular in the treatment of conditions where inhibition of thrombin is required (e.g. thrombosis) or as anticoagulants.

14 Claims, No Drawings

AMIDINO DERIVATIVES AND THEIR USE AS THROMBIN INHIBITORS

FIELD OF THE INVENTION

This invention relates to novel pharmaceutically useful compounds, in particular compounds that are, or are prodrugs of, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

Further, it is known that administration of prodrugs of thrombin inhibitors may give rise to improvements in:
  (a) certain pharmacokinetic properties after administration of; and
  (b) the prevalence of certain side effects associated with, those inhibitors.

Prior Art

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters land amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/03374, WO 96/25426, WO 96/31504, WO 97/02284, WO 97/46577, WO 96/32110, WO 98/06740, WO 97/49404 and WO 98/57932.

However, there remains a need for effective inhibitors of trypsin-like serine proteases, such as thrombin. There is a particular need for compounds which are both orally bioavailable and selective in inhibiting thrombin over other serine proteases. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

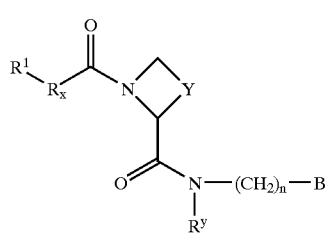

wherein
  $R^1$ represents H, $C_{1-4}$ alkyl (optionally substituted by one or more substituents selected from cyano, halo, OH, $C(O)OR^{1a}$ or $C(O)N(R^{1b})R^{1c}$) or $OR^{1d}$;
  $R^{1d}$ represents H, $C(O)R^{11}$, $SiR^{12}R^{13}R^{14}$ or $C_{1-6}$alkyl, which latter group is optionally substituted or terminated by one or more substituent selected from $OR^{15}$ or $(CH_2)_q R^{16}$;

$R^{12}$, $R^{13}$ and $R^{14}$ independently represent H, phenyl or $C_{1-6}$ alkyl;

$R^{16}$ represents $C_{1-4}$ alkyl, phenyl, OH, $C(O)OR^{17}$ or $C(O)N(H)R^{18}$;

$R^{18}$ represents H, $C_{1-4}$ alkyl or $CH_2C(O)OR^{19}$;

$R^{15}$ and $R^{17}$ independently represent H, $C_{1-4}$ alkyl or $C_{1-3}$ alkylphenyl;

$R^{1a}$, $R^{1b}$, $R^{1c}$, $R^{11}$ and $R^{19}$ independently represent H or $C_{1-4}$ alkyl; and q represents 0, 1 or 2;

$R_x$ represents a structural fragment of formula IIa, IIb or IIc,

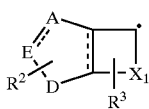

IIa

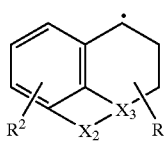

IIb

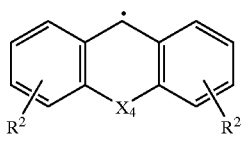

IIc wherein the dotted lines independently represent optional bonds;

A and E independently represent O or S, CH or $CH_2$ (as appropriate), or N or $N(R^{21})$ (as appropriate);

D represents $—CH_2—$, O, S, $N(R^{22})$, $—(CH_2)_2—$, $—CH=CH—$, $—CH_2N(R^{22})—$, $—N(R^{22})CH_2—$, $—CH=N—$, $—N=CH—$, $—CH_2O—$, $—OCH_2—$, $—CH_2S—$ or $—SCH_2—$;

$X_1$ represents $C_{2-4}$ alkylene; $C_{2-3}$ alkylene interrupted by Z; $—C(O)—Z—A^1—$; $—Z—C(O)—A^1—$; $—CH_2—C(O)—A^1—$; $—Z—C(O)—Z—A^2—$; $—CH_2—Z—C(O)—A^2—$; $—Z—CH_2—C(O)—A^2—$; $—Z—CH_2—S(O)_m—A^2—$; $—C(O)—A^3$; $—Z—A^3—$; or $—A^3—Z—$;

$X_2$ represents $C_{2-3}$ alkylene, $—C(O)—A^4—$ or $—A^4—C(O)—$;

$X_3$ represents CH or N;

$X_4$ represents a single bond, O, S, C(O), $N(R^{23})$, $—CH(R^{23})—$, $—CH(R^{23})—CH(R^{24})—$ or $—C(R^{23})=C(R^{24})—$;

$A^1$ represents a single bond or $C_{1-2}$ alkylene;

$A^2$ represents a single bond or $—CH_2—$;

$A^3$ represents $C_{1-3}$ alkylene;

$A^4$ represents C(O) or $C_{1-2}$ alkylene;

Z represents, at each occurrence, O, $S(O)_m$ or $N(R^{25})$;

$R^2$ and $R^4$ independently represent one or more optional substituents selected from $C_{1-4}$ alkyl, $C_{1-4}$ alkoxy (which latter two groups are optionally substituted by one or more halo substituent), methylenedioxy, halo, hydroxy, cyano, nitro, $S(O)_2NH_2$, $C(O)OR^{26}$, $SR^{26}$, $S(O)R^{26a}$, $S(O)_2R^{26a}$ or $N(R^{27})R^{28}$;

$R^3$ represents one or more optional substituents selected from OH, $C_{1-4}$ alkoxy, $C_{1-6}$ alkyl (optionally substituted by one or more halo group), or $N(R^{29a})R^{29b}$;

$R^{25}$, $R^{29a}$ and $R^{29b}$ independently represent H, $C_{1-4}$ alkyl or $C(O)R^{30}$;

$R^{26}$ represents H or $C_{1-4}$ alkyl;

$R^{26a}$ represents $C_{1-4}$ alkyl;

$R^{27}$ and $R^{28}$ independently represent H, $C_{1-4}$ alkyl or $C(O)R^{30}$, or together represent $C_{3-6}$ alkylene, thus forming a 4- to 7-membered ring, which ring is optionally substituted, on a carbon atom that is α to the nitrogen atom, with an $=O$ group;

$R^{21}$, $R^{22}$, $R^{23}$, $R^{24}$ and $R^{30}$ independently represent, at each occurrence, H or $C_{1-4}$alkyl;

Y represents $CH_2$, $(CH_2)_2$, $CH=CH$ (which latter group is optionally substituted by $C_{1-4}$ alkyl), $(CH_2)_3$, $CH_2CH=CH$ or $CH=CHCH_2$ (which latter three groups are optionally substituted by $C_{1-4}$ alkyl, methylene, $=O$ or hydroxy);

$R^y$ represents H or $C_{1-4}$ alkyl;

n represents 0, 1, 2, 3 or 4; and

B represents a structural fragment of formula IIIa, IIIb or IIIc

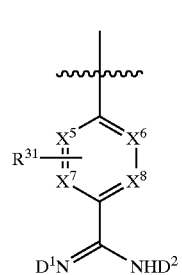

IIIa

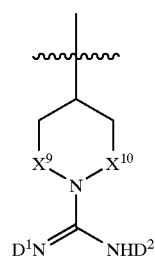

IIIb

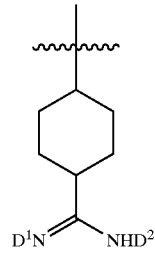

IIIc wherein $X^5$, $X^6$, $X^7$ and $X^8$ independently represent CH, N or N—O;

$X^9$ and $X^{10}$ independently represent a single bond or $CH_2$;

$R^{31}$ represents an optional substituent selected from halo, $C_{1-4}$ alkyl (which group is optionally substituted by one or more halo group), $N(R^{32})R^{33}$, $OR^{34}$ or $SR^{35}$;

$R^{32}$ and $R^{33}$ independently represent H, $C_{1-4}$ alkyl or $C(O)R^{36}$; $R^{34}$, $R^{35}$ and $R^{36}$ independently represent H or $C_{1-4}$ alkyl; and one of $D^1$ and $D^2$ represents H, and the other represents H, $OR^a$, $NHR^a$, $C(=X^{11})X^{12}R^b$, or $D^1$ and $D^2$ together represent a structural fragment of formula IVa:

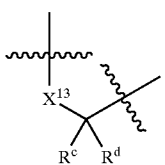

IVa $R^a$ represents H or $—A^5[X^{14}]_n[C(O)]_rR^e$;
$R^b$ represents $—A^5[X^{14}]_n[C(O)]_rR^e$;
$A^5$ represents, at each occurrence, a single bond or $C_{1-12}$ alkylene (which alkylene group is optionally interrupted by one or more O, $S(O)_m$ and/or $N(R^f)$ group, and is optionally substituted by one or more of halo, OH, N(H)C(O) $R^g$, $C(O)N(R^g)R^h$, $C_{3-7}$ cycloalkyl (which cycloalkyl group is optionally interrupted by one or more O, $S(O)_m$ and/or $N(R^f)$ group and/or is optionally substituted by one or more substituents selected from $C_{1-6}$ alkyl, $C_{1-6}$ alkoxy, halo, =O or =S), Het and $C_{6-10}$ aryl (which aryl and Het groups are themselves optionally substituted by one or more substituents selected from $C_{1-6}$ alkyl (optionally substituted by one or more halo substituent), $C_{1-6}$ alkoxy, halo, cyano, $C(O)OR^g$, $C(O)N(R^g)R^h$ and $N(R^f)R^g$));
$R^c$ and $R^d$ both represent H; or one of $R^c$ and $R^d$ represents H or $C_{1-7}$ alkoxy and the other represents $C_{1-7}$ alkyl (which alkyl group is optionally interrupted by one or more O atom); or $R^c$ and $R^d$ together represent $C_{3-8}$ cycloalkyl, which cycloalkyl group is interrupted by one or more O, $S(O)_m$ and/or $N(R^f)$ group;
$R^e$ represents, at each occurrence, H, $C_{1-12}$ alkyl (which alkyl group is optionally interrupted by one or more O, $S(O)_m$ and/or $N(R^f)$ group, and/or is optionally substituted by one or more substituents selected from halo, OH, N(H)C (O)$R^g$ and $C(O)N(R^g)R^h$), $A^7—C_{3-7}$- cycloalkyl (which cycloalkyl group is optionally interrupted by one or more O, $S(O)_m$ and/or $N(R^f)$ group and/or is substituted by one or more substituents selected from $C_{1-6}$ alkyl, $C_{1-6}$ alkoxy, halo, =O and =S), $A^7—C_{6-10}$ aryl or $A^7$-Het (which aryl and Het groups are optionally substituted by one or more substituents selected from $C_{1-6}$ alkyl (optionally substituted by one or more halo substituent), $C_{1-6}$ alkoxy, halo, cyano, $C(O)OR^g$, $C(O N(R^g)R^h$ and $N(R^f)R^g$));
$A^7$ represents a single bond or $C_{1-7}$ alkylene (which alkylene group is optionally interrupted by one or more O, $S(O)_m$ and/or $N(R^f)$ group, and/or are optionally substituted by one or more of halo, OH, $N(H)COR^g$ and $CON(R^g)R^h$);
Het represents, at each occurrence, a five- to ten-membered heteroaryl group, which may be aromatic in character, containing one or more nitrogen, oxygen or sulphur atoms in the ring system;
n and r independently represent 0 or 1;
$X^{11}$, $X^{12}$ and $X^{14}$ independently represent O or S;
$X^{13}$ represents O or $NR^f$;
$R^f$ represents, at each occurrence, H, $C_{1-4}$ alkyl or $C(O)R^g$;
$R^g$ and $R^h$ independently represent, at each occurrence, H or $C_{1-4}$ alkyl; and
m represents, at each occurrence, 0, 1 or 2;
or a pharmaceutically acceptable salt thereof;
provided that:
(a) A and E do not both represent O or S;
(b) E and D do not both represent O or S;
(c) when $R^1$ represents $OR^{1d}$ and $X_1$ represents —C(O)— Z—$A^1$, —Z—$CH_2$—$S(O)_m$—$A^2$— or —Z—C(O)— Z—$A^2$, then $A^1$ or $A^2$ (as appropriate) do not represent a single bond;
(d) when $X_4$ represents $—CH(R^{23})—$, $R^1$ does not represent OH;
(e) when $A^5$ represents a single bond, then n and r both represent 0;
(f) when $A^5$ represents $C_{1-12}$ alkylene, then n represents 1;
(g) when $A^5$ represents $—CH_2—$, n is 1 and r is 0, then $R^e$ does not represent H; and
(h) the compound is not:

(S)- or (R)-1-hydroxy-7-methoxytetralin-1-yl-C(O)-Pro-Pab;
(R)- or (S)-1-hydroxy-7-methoxytetralin-1-yl-C(O)-Pro-Pab;
(S)- or (R)-1-hydroxy-7-methoxytetralin-1-yl-C(O)-Aze-Pab x HOAc;
(R)- or (S)-1-hydroxy-7-methoxytetralin-1-yl-C(O)-Aze-Pab;
1-hydroxy-5-methoxytetralin-1-yl-C(O)-Aze-Pab x HOAc;
1-hydroxy-5,7-dimethyltetralin-1-yl-C(O)-Aze-Pab x HOAc;
1-hydroxy-7-aminotetralin-1-yl-C(O)-Aze-Pab x HOAc;
1-hydroxytetralin-1-yl-C(O)-Aze-Pab x HOAc;
7-methoxytetralin-1-yl-C(O)-Aze-Pab x HOAc;
(R)- or (S)-7-methoxy-1-methyltetralin-1-yl-C(O)-Aze-Pab;,
4-hydroxy-6-methoxychroman-4-yl-C(O)-Aze-Pab x OAc;
(S)- or (R)-1-hydroxy-7-methoxyindan-1-yl-C(O)-Aze-Pab;
1-hydroxy-5-methoxytetralin-1-yl-C(O)-Aze-Pab(OH);
(S)- or (R)-1-hydroxy-7-methoxytetralin-1-yl-C(O)-Aze-Pab(OH);
4-hydroxy-6-methoxychroman-4-yl-C(O)-Aze-Pab(OH);
4-hydroxy-6-methoxychroman-4-yl-C(O)-Aze-Pab(OMe);
(S)- or (R)-1-hydroxy-7-methoxytetralin-1-yl-C(O)-Aze-Pab-(C(O)OCH$_2$CHl$_3$);
(S)- or (R)-1-hydroxy-7-methoxytetralin-1-yl-C(O)-Aze-Pab-(C(O)OCH$_2$CH$_3$);
7-methoxy-1-allyltetralin-1-yl-C(O)Aze-Pab x HOAc;
(S)- or (R)-1-hydroxy-7-chlorotetralin-1-yl-C(O)-Pro-Pab;
1-n-propyl-7-methoxytetralin-1-yl-C(O)-Aze-Pab x HOAc;
6-chloro-4-hydroxychroman-4-yl-C(O)Aze-Pab x HOAc;
4-hydroxychroman-4-yl-C(O)-Aze-Pab x HOAc;
6,8-dichloro-4-hydroxychroman-4-yl-C(O)-Aze-Pab x HOAc;
6-fluoro-4-hydroxychroman-4-yl-C(O)-Aze-Pab x HOAc;
4-hydroxy-6-methylchroman-4-yl-C(O)-Aze-Pab x HOAc;
8-chloro-4-hydroxy-6-methoxychroman-4-yl-C(O)-Aze-Pab x HOAc;
6-chloro-4-hydroxy-8-methylchroman-4-yl-C(O)-Aze-Pab x HOAc;
(S)- or (R)-1-hydroxy-7-methoxytetralin-1-yl-C(O)-Aze-Pab(O-C(O)-i-Pr);
(S)- or (R)-1-hydroxy-7-methoxytetralin-1-yl-C(O)-Aze-Pab(Q-C(O)-Et);

(S)- or (R)-1-hydroxy-7-methoxytetralin-1-yl-C(O)-Aze-Pab(O—C(O)—Ch);
(S)- or (R)-1-hydroxy-7-methoxytetralin-1-yl-C(O)-Aze-Pab(O-allyl);
(S)- or (R)-1-hydroxy-7-methoxytetralin-1-yl-C(O)-Aze-Pab(O-Bzl);
(S)- or (R)-1-hydroxy-7-methoxytetralin-1-yl-C(O)-Aze-Pab-(CO—O-methallyl);
1-hydroxy-7-aminotetralin-1-yl-C(O)-Aze-Pab(OH);
(S)- or (R)-1-hydroxy-7-methoxytetralin-1-yl-C(O)-Aze-Pab(O-Val);
(S)- or (R)-1-hydroxy-7-methoxytetralin-1-yl-C(O)-Aze-(Me)Pab; or
9-hydroxyfluoren-9-yl-C(O)-Aze-Pab x HOAc,
which compounds are referred to hereinafter as "the compounds of the invention".

The compounds of the invention may exhibit tautomerism. All tautomeric forms and mixtures thereof are included within the scope of the invention. Particular tautomeric forms of compounds of the invention that may be mentioned include those connected with the position of the double bond in the amidine functionality in the structural fragment B, and the position of $D^1$ and $D^2$, when one of these does not represent H, Further, it will be appreciated by those skilled in the art that, in the structural fragment of formula IIa, the optional. double bonds, may, in conjunction with certain identities of substituent D, render the ring bearing A, E and D aromatic in character.

The compounds of formula I may also contain one or more asymmetric carbon atoms and may therefore exhibit optical and/or diasteroisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

The term "aryl" includes phenyl, naphthyl and the like. Aryl groups may also be fused to cycloalkyl groups to form e.g. benzo-($C_{3-7}$)-cycloalkyl units (e.g. indanyl, indenyl, tetralinyl, and the like). The term "Het" includes groups such as pyridinyl, thiophenyl, furanyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, quinolinyl, isoquinolinyl, piperidinyl, piperazinyl, chromanyl, thiochromanyl and the like.

Alkyl groups which $R^1$, $R^{1a}$, $R^{1b}$, $R^{1c}$, $R^{1d}$, $R^2$, $R^3$, $R^4$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{26a}$, $R^{27}$, $R^{28}$, $R^{29a}$, $R^{29b}$, $R^{30}$, $R^{31}$, $R^{32}$, $R^{33}$, $R^{34}$, $R^{35}$, $R^{36}$, $R^y$, $R^f$, $R^g$ and $R^h$ may represent, and with which Y, $A^5$ and $R^e$ may be substituted; the alkyl part of alkylphenyl groups which $R^{15}$ and $R^{17}$ may represent; and alkoxy groups which $R^2$, $R^3$, $R^4$, $R^c$ and $R^d$ may represent, and with which $A^5$ and $R^e$ may be substituted, may, when there is a sufficient number of carbon atoms, be linear or branched, saturated or unsaturated, and/or cyclic, acyclic or part cyclic/acyclic. Alkyl groups which $R^c$, $R^d$ and $R^e$ may represent, and alkylene groups which $R^{27}$ and $R^{28}$ (together), $X_1$, $X_2$, $A^1$, $A^3$, $A^4$ and $A^7$ may represent may, when there is a sufficient number of carbon atoms, be linear or branched, and/or saturated or unsaturated. Cycloalkyl groups which $R^c$ and $R^d$ may together represent, and which $R^e$ may include, may be branched and/or may be saturated or unsaturated.

Alkylene groups which $A^5$ may represent may, when there is a sufficient number of carbon atoms, be linear or branched, be saturated or unsaturated, and/or be cyclic, acyclic or part cyclic/acyclic. The $C_{3-7}$ cycloalkyl group with which $A^5$ may be substituted, may be branched, saturated or unsaturated, and/or part cyclic/acyclic. This cycloalkyl group may also be attached to $A^5$ via a carbon-carbon bond or may be attached directly to the alkylene chain (i.e. to give a "spiro" compound).

Halo groups, which $R^2$, $R^4$ and $R^{31}$ may represent, and with which $R^1$, $R^2$, $R^3$, $R^4$, $R^{31}$, $A^5$, $R^e$ and $A^7$ may be substituted, include fluoro, chloro, bromo and iodo.

In the structural fragments of formulae IIa, IIb and IIc, the dots indicate the carbon atom which is bonded to the —C(O)— group and to $R^1$ in a compound of formula I (for the avoidance of doubt, there is no further H atom bonded to the carbon atom so indicated).

The wavy lines on the bond in the fragments of formulae IIIa, IIIb, IIIc, IVa and Ar (below) signify the bond position of the fragment.

Abbreviations are listed at the end of this specification.

Preferred compounds of the invention include those in which, when:

$R^2$ and $R^4$ do not independently represent $C_{1-4}$ alkoxy substituted by one or more halo substituent, $SR^{26}$, $S(O)R^{26a}$, $S(O)_2R^{26a}$ or $N(R^{27})R^{28}$, in which $R^{27}$ and $R^{28}$ independently represent $C(O)R^{30}$, or together represent $C_{3-6}$ alkylene, thus forming a 4- to 7-membered ring, which ring is optionally substituted, on a carbon atom that is α to the nitrogen atom, with a =O group, and $R^{26}$, $R^{26a}$ and $R^{30}$ are as hereinbefore defined;

$R^3$ does not represent one or more optional substituents selected from $C_{1-6}$ alkyl (optionally substituted by one or more halo group) or $N(R^{29a})R^{29b}$, in which $R^{29a}$ and $R^{29b}$ are as hereinbefore defined;

$R^{25}$ does not represent $C(O)R^{30}$, in which $R^{30}$ is as hereinbefore defined;

Y does not represent CH=CH substituted by $C_{1-4}$ alkyl; and/or $R^{31}$ does not represent $C_{1-4}$ alkyl (substituted by one or more halo group), $N(R^{32})R^{33}$, $OR^{34}$ or $SR^{35}$, in which $R^{32}$, $R^{33}$, $R^{34}$ and $R^{35}$ are as hereinbefore defined, (i.e. when the values of $R^2$, $R^4$, $R^3$, $R^{25}$, Y and $R^{31}$ are other than those listed immediately above)

then (i) $D^1$ and $D^2$ do not both represent H;

(ii) when $D^1$ or $D^2$ represents $OR^a$, then $R^a$ does not represent H, phenyl, benzyl or $C_{1-7}$ alkyl (which latter group is optionally interrupted by O or is optionally substituted by halo);

(iii) when $D^1$ or $D^2$ represents $C(X^{11})X^{12}R^b$ and $X^{11}$ and $X^{12}$ both represent O, then $R^b$ does not represent 2-naphthyl, phenyl, $C_{1-3}$ alkylphenyl (which latter three groups are optionally substituted by $C_{1-6}$ alkyl, $C_{1-6}$ alkoxy or halo); $C_{1-12}$ alkyl (which latter group is optionally substituted by $C_{1-6}$ alkoxy, $C_{1-6}$ acyloxy or halo); —$[C(R^q)(R^r)]_pOC(O)R^s$, in which p is 1, 2 or 3, $R^q$ and $R^r$ independently represent H or $C_{1-6}$ alkyl (provided that the total number of carbon atoms in $[C(R^q)(R^r)]_p$ does not exceed 12), and $R^s$ represents $C_{1-6}$ alkyl (optionally substituted by $C_{1-6}$ alkoxy), $C_{1-12}$ alkyl (optionally substituted by halo), $C_{3-7}$ cycloalkyl, phenyl, naphthyl or $C_{1-3}$ alkylphenyl (which latter four groups are optionally substituted by $C_{1-6}$ alkyl or halo); or —$CH_2$-Ar, in which Ar represents the structural fragment:

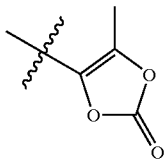

Compounds of the invention which may be mentioned include those in which:

$R^2$ and $R^4$ independently represent $C_{1-4}$ alkoxy substituted by one or more halo substituents, $SR^{26}$, $S(O)R^{26a}$, $S(O)_2R^{26a}$ or $N(R^{27})R^{28}$, in which $R^{27}$ and $R^{28}$ independently represent $C(O)R^{30}$, or together represent $C_{3-6}$ alkylene, thus forming a 4- to 7-membered ring, which ring is optionally substituted, on a carbon atom that is α to the nitrogen atom, with a =O group, and $R^{26}$, $R^{26a}$ and $R^{30}$ are as hereinbefore defined;

$R^3$ represents one or more optional substituents selected from $C_{1-6}$ alkyl (optionally substituted by one or more halo group) or $N(R^{29a})R^{29b}$, in which $R^{29a}$ and $R^{29b}$ are as hereinbefore defined;

$R^{25}$ represents $C(O)R^{30}$, in which $R^{30}$ is as hereinbefore defined;

Y represents CH=CH substituted by $C_{1-4}$ alkyl;

$R^{31}$ represents $C_{1-4}$ alkyl (substituted by one or more halo group), $N(R^{32})R^{33}$, $OR^{34}$ or $SR^{35}$, wherein $R^{32}$, $R^{33}$, $R^{34}$ and $R^{35}$ are as hereinbefore defined.

Further compounds of the invention which may be mentioned include those in which:

(i) when one of $D^1$ or $D^2$ represents $OR^a$, then $R^a$ does not represent H, phenyl, benzyl or $C_{1-7}$ alkyl (which latter group is optionally interrupted by O or is optionally substituted by halo);

(ii) when one of $D^1$ or $D^2$ represents $C(X^{11})X^{12}R^b$ and $X^{11}$ and $X^{12}$ both represent O, then $R^b$ does not represent 2-naphthyl, phenyl, $C_{1-3}$ alkylphenyl (which latter three groups are optionally substituted by $C_{1-6}$ alkyl, $C_{1-6}$ alkoxy or halo); $C_{1-12}$ alkyl (which latter group is optionally substituted by $C_{1-6}$ alkoxy, $C_{1-6}$ acyloxy or halo); —$[C(R^q)(R^r)]_pOC(O)R^s$, in which p is 1, 2 or 3, $R^q$ and $R^r$ independently represent H or $C_{1-6}$ alkyl (provided that the total number of carbon atoms in $[C(R^q)(R^r)]_p$ does not exceed 12), and $R^s$ represents $C_{1-6}$ alkyl (optionally substituted by $C_{1-6}$ alkoxy), $C_{1-12}$ alkyl (optionally substituted by halo), $C_{3-7}$ cycloalkyl, phenyl, naphthyl or $C_{1-3}$ alkylphenyl (which latter four groups are optionally substituted by $C_{1-6}$ alkyl or halo); or —$CH_2$-Ar, in which Ar represents the structural fragment:

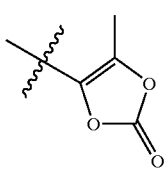

When n represents 2 and B represents a structural fragment of formula IIIb, preferred compounds of the invention include those wherein $X^9$ and $X^{10}$ do not both represent $CH_2$.

Preferred compounds of formula I include those wherein:

$R^1$ represents OH or $C_{1-4}$ alkyl (which latter group is optionally substituted by cyano or OH);

$R_x$ represents a structural fragment of formula IIb or, especially, IIa;

when $R_x$ represents a structural fragment of formula IIa, the dotted lines represent bonds, A and E both represent CH and D represents —CH=CH—;

when $R_x$ represents a structural fragment of formula IIa, $X_1$ represents optionally unsaturated $C_2$- or $C_3$-alkylene, or —Z—$A^3$ (in which Z represents O, $S(O)_m$ or $N(R^{25})$ (in which $R^{25}$ is as hereinbefore defined or represents $C_{1-4}$ alkyl or $C(O)R^{30}$ and m and $R^{30}$ are as hereinbefore defined) and $A^3$ represents $C_1$- or $C_2$-alkylene (which latter group is optionally unsaturated));

Y represents $(CH_2)_3$, preferably $(CH_2)_2$ and more preferably $CH_2$;

B represents a structural fragment of formula IIIa in which $X^5$, $X^6$, $X^7$ and $X^8$ all represent CH.

Particularly preferred compounds of the invention include those wherein, when $R_x$ represents a structural fragment of formula IIa, $X_1$ represents $C_3$-alkylene or —$Z(CH_2)_2$—, in which Z represents $S(O)_m$, $N(R^{25})$ (in which $R^{25}$ is as hereinbefore defined) or, especially, O.

When $R_x$ represents a structural fragment of formula IIa, and $R^2$ represents at least one substituent, a preferred point of substitution is at the carbon atom which is at position E. It is preferred that at least one (and preferably two) substituents $R^2$ are present in a structural fragment of formula IIa.

When $R_x$ represents a structural fragment of formula IIa, the dotted lines represent bonds, A and E both represent CH and D represents —CH=CH— (i.e. the ring bearing $R^2$ is a benzo group), and $R^2$ represents at least one substituent, the ring is preferably substituted either at the carbon atom in the —CH=CH— group (position D) which is adjacent to the ring junction, or at the carbon atom which is at position E, or preferably at both of these sites. For example, when the fragment IIa represents a tetralin-1-yl group (i.e. the dotted lines represent bonds, A and E both represent CH, D represents —CH=CH— and $X_1$ represents saturated $C_3$-alkylene), preferred substitution positions are the 5- and 7-positions, or, preferably, di-substitution at both of these positions. Correspondingly, when the fragment IIa represents a chroman-4-yl, a thiochroman-4-yl, or a quinolin-4-yl, group (i.e. the dotted lines represent bonds, A and E both represent CH, D represents —CH=CH—, and $X_1$ represents —$Z(CH_2)_2$—, in which Z represents O, $S(O)_m$ or $N(R^{25})$), preferred substitution positions are the 8- and 6-positions, or, preferably, di-substitution at both of these positions.

Preferred optional substituents $R^2$ include halo, $C_{1-4}$ alkyl, $C_{1-4}$ alkoxy (which latter two groups are optionally substituted by one or more halo groups) or $N(R^{27})R^{28}$.

When $R^1$ represents OH, $R_x$ represents an unsubstituted (by $R^2$ and $R^4$) structural fragment of formula IIc, in which $X_4$ represents a single bond, $CH_2$ or O, Y represents $CH_2$ or $(CH_2)_2$, $R^y$ represents H and n represents 1, preferred compounds of the invention include those in which B does not represent a structural fragment of formula IIIb in which $X^9$ and $X^{10}$ are both $CH_2$ and $D^1$ and $D^2$ are both H.

When $D^1$ and $D^2$ together represent a structural fragment of formula IVa, in which $X^{13}$ is O, preferred compounds of the invention include those in which one of $R^c$ and $R^d$ represents H or $C_{1-7}$ alkoxy and the other represents $C_{1-7}$ alkyl (e.g. $C_{1-4}$ alkyl, including linear, saturated, unsubstituted, and uninterrupted, $C_{1-4}$ alkyl).

When $D^1$ or $D^2$ represents $OR^a$ and $R^a$ represents $—A^5[X^{14}]_n[C(O)]_rR^e$, and:

(i) $A^5$ is a single bond (and thus n and r both represent 0), preferred compounds of the invention include those in which $R^e$ is:
  (1) optionally substituted $A^7$-aryl, in which $A^7$ is preferably a single bond or $C_{1-3}$ alkylene (e.g. $C_{1-2}$-alkylene) and aryl is preferably $C_{6-10}$-aryl, (e.g. phenyl), which $A^7$-aryl group is optionally substituted by one or more halo, $C_{1-6}$ alkoxy (e.g. $C_{1-4}$ alkoxy, such as methoxy), $C_{1-6}$ alkyl (e.g. $C_{1-4}$ alkyl) or a haloalkyl (e.g. $CF_3$) substituent);
  (2) H or linear, branched, optionally unsaturated, and/or cyclic, $C_{1-12}$ alkyl (e.g. $C_{3-7}$ alkyl), which cyclic alkyl group is optionally interrupted by an O atom and, optionally, a further O atom or $S(O)_m$ group;
(ii) $A^5$ is linear or branched $C_{1-2}$ alkylene, $X^{14}$ is O and r is 0, preferred compounds of the invention include those in which $R^e$ is $C_{1-3}$ alkyl or $A^7$-aryl, in which $A^7$ is a single bond and the aryl group is preferably optionally substituted phenyl.

When $D^1$ or $D^2$ represents $OR^a$, preferred compounds of the invention include those in which $R^a$ is H or $C_{1-4}$ alkyl.

When $D^1$ or $D^2$ represents $—C(=X^{11})X^{12}R^b$, in which $X^{11}$ represents O and $X^{12}$ represents O or S, and, in which $R^b$ group, $A^5$ represents a single bond (and thus n and r both represent 0), preferred compounds of the invention include those in which $R^e$ represents optionally unsaturated $C_{1-6}$ (e.g. $C_{1-4}$) alkyl, $A^7$—$C_{6-10}$-aryl (in which $A^7$ represents a single bond or $C_{1-2}$ alkylene and the $C_{6-10}$ aryl group is preferably phenyl, which $A^7$—$C_{6-10}$-aryl group is optionally substituted by one or more halo, $C_{1-4}$ alkyl and/or $C_{1-4}$ alkoxy groups), or $A^7$—$C_{3-7}$-cycloalkyl (especially $A^7$—$C_{4-5}$ cycloalkyl), in which $A^7$ represents a single bond or linear or branched $C_{1-7}$ alkylene, and which cycloalkyl group is optionally substituted by $C_{1-3}$ alkyl.

Compounds of formula I in which the fragment

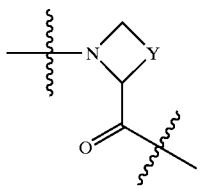

is in the S-configuration are preferred. The wavy lines on the bonds in the above fragment signify the bond position of the fragment.

Preferred compounds of formula I include the compounds of the Examples described hereinafter.

Preparation

According to the invention there is also provided a process for the preparation of compounds of formula I which comprises:

(i) the coupling of a compound of formula IV,

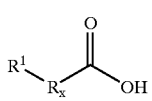

IV wherein $R^1$ and $R_x$ are as hereinbefore defined with a compound of formula V,

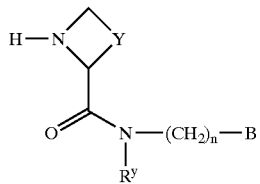

V wherein $R^y$, Y, n and B are as hereinbefore defined, for example in the presence of a coupling agent (e.g. oxalyl chloride in DMF, PyBOP, EDC, DCC, HBTU, HATU or TBTU), an appropriate base (e.g. pyridine, 2,4,6-trimethylpyridine, 2,4,6-collidine, DMAP, TEA or DIPEA) and a suitable organic solvent (e.g. dichloromethane, acetonitrile or DMF);

(ii) the coupling compound of formula VI,

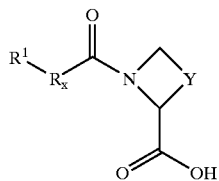

VI wherein $R^1$, $R_x$ and Y are as hereinbefore defined with a compound of formula VII,

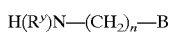

(VII)

wherein $R^y$, n and B are as hereinbefore defined, for example in the presence of a coupling agent (e.g. oxalyl chloride in DMF, PYBOP, EDC, DCC, HBTU, HATU or TBTU), an appropriate base (e.g. pyridine, 2,4,6-trimethylpyridine, 2,4,6-collidine, DMAP, TEA or DIPEA) and a suitable organic solvent (e.g. dichloromethane, acetonitrile or DMF);

(iii) for compounds of formula I in which $D^1$ or $D^2$ represents $OR^a$ or $NHR^a$, reaction of a compound of formula VIII,

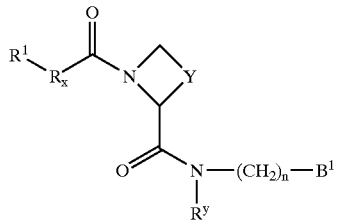

VIII wherein $B^1$ represents a structural fragment of formula IIId, IIIe or IIIf

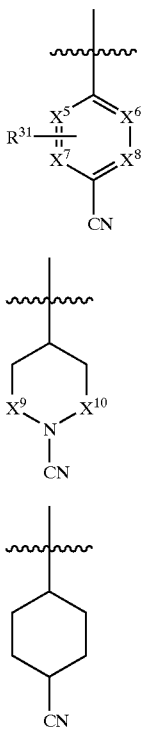

IIId

IIIe

IIIf and $R^1$, $R_x$, $Y$, $R^y$, n, $R^{31}$, $X^5$, $X^6$, $X^7$, $X^8$, $X^9$ and $X^{10}$ are as hereinbefore defined with a compound of formula IX,

$H_2NX^aR^a$   IX wherein $X^a$ represents O or NH and $R^a$ is as hereinbefore defined, for example at between 40 and 70° C. (e.g. 60°), in the presence (optionally) of a suitable base (e.g. TEA), and an appropriate organic solvent (e.g. THF, $CH_3CN$, DMF or DMSO), and, optionally, wherein the compound of formula VIII is first treated with gaseous HCl, in the presence of a lower alkyl alcohol (e.g. ethanol) at, for example, 0° C.;

(iv) for compounds of formula I in which $D^1$ or $D^2$ represents $OR^a$ or $NHR^a$, reaction of a compound of formula I in which $D^1$ or $D^2$ (as appropriate) represents $C(O)OR^{b1}$, in which $R^{b1}$ represents a protecting group (such as a 2-trimethylsilylethyl, a suitable alkyl (e.g. $C_{1-6}$ alkyl), or alkylphenyl (e.g. benzyl), group) with a compound of formula IX as hereinbefore defined, for example under similar reaction conditions to those described hereinbefore for preparation of compounds of formula I (step (iii)) (the skilled person will appreciate that in such a reaction the diprotected (i.e. $C(O)OR^{b1}$ and $OR^a/NHR^a$ protected) derivative may, in some cases, be isolated if desired, and the $C(O)OR^{b1}$ group then removed using conventional techniques);

(v) for compounds of formula I in which $D^1$ or $D^2$ represents $OR^a$ or $NHR^a$, $R^a$ represents $-A^5[X^{14}]_n[C(O)]_rR^e$, in which $A^5$ does not represent a single bond, and n represent 1, reaction of a compound of formula I in which $D^1$ or $D^2$ (as appropriate) represents OH or $NH_2$, with a compound of formula X,

$L^1A^{5a}[X^{14}][C(O)]_rR^e$   X wherein $L^1$ represents a suitable leaving group, such as lower alkoxy or halo, $A^{5a}$ represents $A^5$, as hereinbefore defined except that it does not represent a single bond, and $X_{14}$, r and $R^e$ are as hereinbefore define, for example under conditions that are well known to those skilled in the art (see e.g. U.S. Pat. No. 3,822,283);

(vi) for compounds of formula I in which $D^1$ or $D^2$ represents $OR^a$ or $NHR^a$, $R^a$ represents $-A^5[X^{14}]_n[C(O)]_rR^e$, in which $A^5$ represents $C_{2-12}$ alkylene, which alkylene group is branched at the carbon atom that is α to the O or N atom of $OR^a$ or $NHR^a$ (as appropriate), and which group is optionally branched at the carbon atom that is β to that atom, n represents 1, r represents 0 and $R^e$ is as hereinbefore defined, reaction of a compound of formula I in which $D^1$ or $D^2$ (as appropriate) represents OH or $NH_2$, with a compound of formula XI,

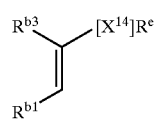

XI or a geometrical isomer thereof, or a mixture of such geometrical isomers, in which $R^{b1}$ and $R^{b3}$ each represent H or an alkyl group, provided that the total number of carbon atoms provided by $R^{b1}$ and $R^{b3}$ does not exceed 10, and wherein $X^{14}$ and $R^e$ are as hereinbefore define, for example under conditions that are well known to those skilled in the art;

(vii) for compounds of formula I in which $D^1$ or $D^2$ represents $OR^a$ or $NHR^a$, $R^a$ represents $-A^5[X^{14}]_n[C(O)]_rR^e$, in which $A^5$ represents a single bond (and thus n and r both represent 0), and $R^e$ represents $A^7$—$C_{3-6}$-cycloallyl, in which $A^7$ represents a single bond, and the cycloalkyl group is interrupted by at least one O or S atom, which atom is between the carbon atom at the point of attachment to the O or NH group of $OR^a$ or $NHR^a$, and a carbon atom that is α to that point of attachment, and which cycloalkyl group is optionally interrupted by one or more O or $S(O)_m$ group and/or optionally substituted by one or more =O group, reaction of a compound of formula I, in which $D^1$ or $D^2$ (as appropriate) represents OH or $NH_2$, with a compound of formula XII,

XII wherein $X^{15}$ represents O or S and $X^{16}$ represents $C_{1-4}$ alkylene (which alkylene group is optionally interrupted by one or more O or $S(O)_m$ group and/or optionally substituted by one or more =O group), for example under conditions that are well known to those skilled in the art;

(viii) for compounds of formula I in which $D^1$ or $D^2$ represents $C(X^{11})X^{12}R^b$, reaction of a compound of formula I in which $D^1$ and $D^2$ both represent H with a compound of formula XIII,

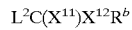
$L^2C(X^{11})X^{12}R^b$   XIII wherein $L^2$ represents a suitable leaving group, such as halo or p-nitrophenoxy, and $X^{11}$, $X^{12}$ and $R^b$ are as hereinbefore define, for example 0° C. in the presence of a suitable base (e.g. NaOH) and an appropriate organic solvent (e.g. THF) or water;

(ix) for compounds of formula I in which $D^1$ and $D^2$ together represent a structural fragment of formula IVa, reaction of a corresponding compound of formula I in which $D^1$ or $D^2$ represents OH or $NHR^f$ (in which $R^f$ is as hereinbefore defined), with a compound of formula XV, $$(R^c)(R^d)C(R^{c1})(R^{c2}) \quad\quad\quad XV$$

wherein $R^{c1}$ and $R^{c2}$ both represent $-OR^{c3}$, in which $R^{c3}$ represents $C_{1-3}$ alkyl, or together represent =O, and $R^c$ and $R^d$ are as hereinbefore defined, for example by using the compound of formula XV as solvent and HCl as a catalyst, at between room temperature and reflux (see e.g. *J. Org. Chem. USSR*, 21, 177 (1985));

(x) for compounds of formula I in which one or more of $X^5$, $X^6$, $X^7$ and $X^8$ represent N—O, oxidation of a corresponding compound of formula I in which $X^5$, $X^6$, $X^7$ and/or $X^8$ (as appropriate) represent(s) N under conditions that are well known to those skilled in the art (for example in the presence of a suitable oxidising agent (e.g. mCPBA), at an appropriate temperature (e.g. 0° C.), and in the presence of a suitable organic solvent (e.g. DCM));

(xi) for compounds of formula I in which any one of Z, $X_1$, $R^2$, $R^4$, $A^5$, $A^7$, $R^c$, $R^d$ and/or $R^e$ comprises or includes a S(O) or a $S(O)_2$ group, oxidation of a corresponding compound of formula I (or a compound corresponding to a compound of formula I) wherein Z, $X_1$, $R^2$, $R^4$, $A^5$, $A^7$, $R^c$, $R^d$ and/or $R^e$ (as appropriate) comprise(s) or include(s) a S group, in the presence of an appropriate amount of a suitable oxidising agent (e.g. mCPBA) and an appropriate organic solvent; or (xii) for compounds of formula I in which $D^1$ and $D^2$ both represent H, removal of a $OR^a$, $NHR^a$ or $C(=X^{11}) X^{12}R^b$ group (in which $R^a$, $R^b$, $X^{11}$ and $X_{12}$ are as hereinbefore defined), or removal of a structural fragment of formula IVa as hereinbefore defined, from a corresponding compound of formula I (i.e. deprotection) under conditions known to those skilled in the art.

Compounds of formula IV are commercially available, are well known in the literature, or are available using known and/or standard techniques.

For example, compounds of formula IV in which $R^1$ represents OH may be prepared by reaction of a compound of formula XVI, $$R_x=O \quad\quad\quad XVI$$

wherein $R_x$ is as hereinbefore defined, with:

(a) KCN, for example at 20° C. in the presence of sodium bisulphite in water, followed by hydrolysis in the presence of aqueous acid (e.g. HCl), for example at 20° C. in the presence of a suitable solvent (e.g. alcohol and/or water);

(b) $CHCl_3$, in the presence of aqueous base (e.g. NaOH);

(c) TMSCN, for example at 20° C. in the presence of a suitable organic solvent (e.g. $CH_2Cl_2$), followed by hydrolysis in the presence of acid (e.g. HCl or $H_2SO_4$), for example at 20° C. (e.g. according, or analogously, to the method described by Bigge et al in *J. Med. Chem.* (1993) 36, 1977), followed by alkaline hydrolysis to give the free acid.

Compounds of formula IV in which $R^1$ represents OH may alternatively be prepared by way of a Sharpless stereoselective dihydroxylation of a compound of formula XVIA, $$R_x=CH_2 \quad\quad\quad XVIA$$

wherein $R_x$ is as hereinbefore define, under conditions known to those skilled in the art (e.g. at low temperature (e.g. 0° C.), using, for example, the commercial reagent AD-mix-β™ in the presence of suitable solvent (e.g. t-butanol), followed by oxidation of the resultant intermediate (e.g. at elevated temperature (e.g. 75° C.) in the presence of a stream of air and Pt/C (5%) in acetone/water).

Compounds of formula IV in which $R^1$ represents H may be prepared from corresponding compounds of formula IV in which $R^1$ represents OH (or a lower alkyl ester of the acid), for example by elimination of water, followed by hydrogenation of the resultant alkene using techniques which are well known to those skilled in the art, followed by, if necessary, hydrolysis to give the free acid.

Compounds of formula IV in which $R^1$ represents $C_{1-4}$ alkyl may be prepared from corresponding compounds of formula IV in which $R^1$ represents H (or a lower alkyl ester of the acid), for example by reaction with an appropriate alkyl halide using techniques which are well known to those skilled in the art, followed by, if necessary, hydrolysis to give the free acid.

Compounds of formula IV in which $R^1$ represents $OR^{1d}$ and $R^{1d}$ represents $C(O)R^{11}$, $SiR^{12}R^{13}R^{14}$ or $C_{1-6}$ alkyl may be prepared by acylation, silylation or alkylation (as appropriate) of a corresponding compound of formula IV in which $R^1$ represents OH (or a lower alkyl ester of the acid) under conditions which are well known to those skilled in the art, followed by, if necessary, hydrolysis to give the free acid.

Compounds of formula V may be prepared by reaction of a compound of formula XVII

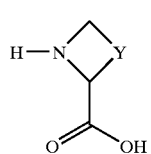

XVII wherein Y is as hereinbefore defined with a compound of formula VII as hereinbefore defined, for example under conditions such as those described hereinbefore for synthesis of compounds of formula I.

Compounds of formulae V and VII in which $R^y$ represents $C_{1-4}$ alkyl may be prepared by reaction of a corresponding compound of formula V or formula VII, as appropriate, in which $R^y$ represents H with a compound of formula XVIII, $$R^yHal \quad\quad\quad XVIII$$

wherein Hal represents halo (e.g. Cl, Br or I) and $R^y$ is as hereinbefore defined, for example under conditions which are well known to those skilled in the art.

Compounds of formula VI are readily available using known techniques. For example, compounds of formula VI may be prepared by reaction of a compound of formula IV as hereinbefore defined with a compound of formula XVII as hereinbefore defined, for example under conditions such as those described hereinbefore for synthesis of compounds of formula I.

Compounds of formula VIII may be prepared in accordance with peptide coupling techniques, for example in analogous fashion to the methods described hereinbefore for compounds of formula I.

Compounds of formula XVI are commercially available, are well known in the literature, or may be prepared in accordance with known techniques. For example compounds of formula XVI may be prepared as follows:

(a) Compounds of formula XVI in which $R_x$ represents a structural fragment of formula IIa, in which the dotted lines represent bonds, A and E both represent CH and D represents —CH=CH—; $X_1$ represents $C_{2-4}$ alkylene, —Z—$A^3$— or —C(O)—$A^3$—, in which Z and $A^3$ are as hereinbefore defined; and $R^3$ is absent, may be prepared by cyclisation of a compound of formula XIX,

XIX wherein $X_{1a}$ represents $C_{2-4}$ alkylene, —Z—$A^3$— or —C(O)—$A^3$—, and Z, $A^3$ and $R^2$ are as hereinbefore defined, using an appropriate acylating agent, for example at 100° C. in the presence of polyphosphoric acid or using $PCl_5$ followed by $AlCl_3$, or at low temperature (e.g. 5° C.) in the presence of boron trifluoride dimethyl etherate and/or trifluoroacetic anhydride and an appropriate solvent (e.g. $CH_2Cl_2$). Compounds of formula XIX in which $X_{1a}$ represents $C_3$-alkylene or —C(O)—$A^3$—, in which $A^3$ represents $C_2$-alkylene, may be prepared in accordance with known techniques, for example by reaction of succinic anhydride with the corresponding phenyl lithium and, for compounds of formula XIX in which $X_{1a}$ represents $C_3$-alkylene, selective reduction of the resultant ketone, under conditions which are well known to those skilled in the art. Compounds of formula XIX in which $X_{1a}$ represents —Z—$A^3$— and $A^3$ represents $C_{2-3}$ alkylene may be prepared as described hereinafter.

(b) Compounds of formula XVI in which $R_x$ represents a structural fragment of formula IIa, in which the dotted lines represent bonds, A and E both represent CH and D represents —CH=CH—; $X_1$ represents $C_{2-4}$ alkylene or —C(O)—$A^3$—, in which $A^3$ is as hereinbefore defined; and $R^3$ is absent, may alternatively be prepared by cyclisation of a compound of formula XX,

XX wherein R represents $C_{1-6}$ alkyl and $X_{1a}$ and $R^2$ are as hereinbefore defined, for example at 20° C. in the presence of a suitable base (e.g. an alkali metal alkoxide) and an appropriate organic solvent (e.g. lower alkyl alcohol) followed by hydrolysis and decarboxylation. Compounds of formula XX may be prepared in accordance with known techniques. For example, compounds of formula XX in which $X_{1a}$ represents $C_3$-alkylene or —C(O)—$A^3$— in which $A^3$ represents $C_2$-alkylene may be prepared by reaction of succinic anhydride with a compound of formula XXI,

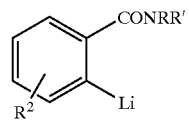

XXI wherein R' represents $C_{1-6}$ alkyl and R and $R^2$ are as hereinbefore defined and, for compounds of formula XX in which $X_{1a}$ represents $C_3$-alkylene, selective reduction of the resultant ketone, followed by functional group transformations of the amide and the acid to ester groups, under conditions which are well known to those skilled in the art.

(c) Compounds of formula XVI in which $R_x$ represents a structural fragment of formula IIa, in which the dotted lines represent bonds, A and E both represent CH and D represents —CH=CH—; $X_1$ represents —Z—$A^3$— in which $A^3$ represents $C_2$ alkylene and Z represents O or S; and $R^3$ is absent, may be prepared by cyclisation of a compound of formula XXII,

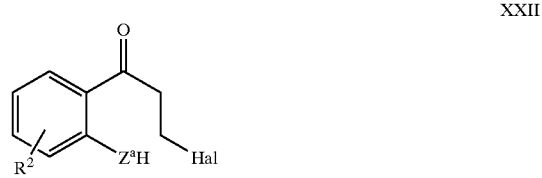

XXII wherein $Z^a$ represents O or S and Hal and $R^2$ are as hereinbefore defined, for example at 20° C. in the presence of aqueous-ethanolic NaOH, For to corresponding compounds of formula XVI in which $X_1$ represents —Z—$A^3$— and Z represents $S(O)_m$ in which m is 1 or 2, this above-mentioned cyclisation should be followed by carrying out an oxidation reaction on the cyclised product comprising an S atom, for example using m-chloroperbenzoic acid.

(d) Compounds of formula XVI in which $R_x$ represents a structural fragment of formula IIa, in which the dotted lines represent bonds, A and E both represent CH and D represents —CH=CH—; $X_1$ represents —Z—$A^3$— (in which $A^3$ represents $C_2$-alkylene) or —Z—C(O)—$A^1$ (in which $A^1$ represents $C_1$-alkylene); and $R^3$ is absent, may be prepared by reaction of a compound of formula XXIII,

XXIII wherein $R^2$ and Z are as hereinbefore defined, with either:

(1) for compounds of formula XVI in which $X_1$ represents —Z—$A^3$— in which $A^3$ represents $C_2$-alkylene, a compound of formula XXIV,

$H_2C$=CH—$CO_2R$     XXIV wherein R is as hereinbefore defined, for example at 20° C. in the presence of a suitable base (e.g. triethylamine or sodium ethoxide) and an appropriate organic solvent (e.g. ethanol or DMF); or (2) a compound of formula XXV,

    XXV wherein $L^1$ represents a suitable leaving group (such as Cl, Br, I, mesylate or tosylate), G represents $CH_2$ or C(O) and R is as hereinbefore defined, for example at 20° C. in the presence of a suitable base (e.g. triethylamine) and an appropriate organic solvent (e.g. THF); followed by cyclisation under appropriate conditions (e.g. those described hereinbefore).

(e) Compounds of formula XVI in which $R_x$ represents a structural fragment of formula IIa, in which the ring bearing A, E and D is a carbocyclic aromatic, or heterocyclic aromatic, ring as defined hereinbefore in respect of compounds of formula I; $X^1$ represents —$CH_2$—Z—$C_{1-2}$ alkylene-, in which Z is as hereinbefore defined; and $R^3$ is absent, may be prepared by reaction of a compound of formula XXVI,

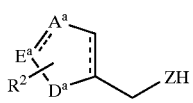    XXVI wherein the ring bearing $A^a$, $E^a$ and $D^a$ is a carbocyclic aromatic, or heterocyclic aromatic, ring as define hereinbefore in respect of compounds of formula I, and Z and $R^2$ are as hereinbefore defined, with a compound of formula XXVII,

    XXVII wherein Alk represents $C_{1-2}$ alkylene and $L^1$ is as hereinbefore defined, for example at 20° C. in the presence of a suitable base (e.g. sodium methoxide) and an appropriate organic solvent (e.g. THF).

(f) Compounds of formula XVI in which $R_x$ represents a structural fragment of formulae IIb, IIc or IIa, in which latter case the ring bearing A, E and D is a carbocyclic aromatic, or heterocyclic aromatic, ring as defined hereinbefore in respect of compounds of formula I; and, in the cases when $R_x$ represents a structural fragment of formulae IIa or IIb, $R^3$ is absent, may be prepared by cyclisation of a compound of formula XXIX,

    XXIX wherein $R_{xa}$ represents a structural fragment of formula XXIXa, XXIXb or XXIXc

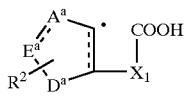    XXIXa

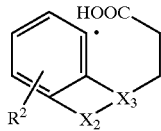    XXIXb

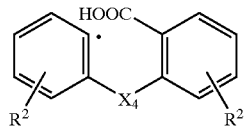    XXIXc wherein, in XXIXa, the ring bearing $A^a$, $E^a$ and $D^a$ is a carbocyclic aromatic, or heterocyclic aromatic, ring as defined hereinbefore in respect of compounds of formula I, and $R^2$, $R^4$, $X_1$, $X_2$, $X_3$ and $X_4$ are as hereinbefore defined, in the presence of polyphosphoric acid, for example at 100° C. The dots adjacent to the carbon atoms in fragments of formula XXIXa, XXIXb and XXIXc signify the point of attachment of the fragments to the $CO_2H$ group of the compound of formula XXIX. Compounds of formula XXIX may be prepared by hydrolysis of a corresponding compound of formula XXX,

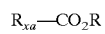    XXX wherein $R_{xa}$ and R are as hereinbefore defined (and in which the $CO_2H$ in the fragments of formulae XXIXa, XXIXb and XXIXc in $R_{xa}$ may also be replaced by $CO_2R$), for example under reaction conditions which are well known to those skilled in the art.

(g) Compounds of formula XVI in which $R_x$ represents a structural fragment of formula IIa in which the ring bearing A, E and D is a carbocyclic aromatic, or heterocyclic aromatic, ring as defined hereinbefore in respect of compounds of formula I; $X^1$ represents —$OCH_2$—; and $R^3$ is absent, may be prepared by reaction of a compound of formula XXXI,

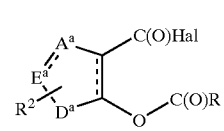    XXXI wherein the ring bearing $A^a$, $E^a$ and $D^a$ is a carbocyclic aromatic, or heterocyclic aromatic, ring as defined hereinbefore in respect of compounds of formula I, and $R^2$, Hal and R are as hereinbefore defined, with diazomethane, for example at 20° C. in the presence of a suitable organic solvent (e.g. diethyl ether).

(h) Compounds of formula XVI in which $R_x$ represents a structural fragment of formula IIa, in which the dotted lines represent bonds, A and E both represent CH and D represents —CH=CH—; $X_1$ represents —C(O)—O—$CH_2$—; and $R^3$ is absent, may be prepared by cyclisation of a compound of formula XXXII,

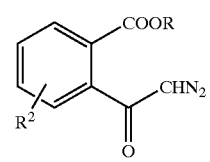    XXXII wherein $R^2$ and R are as hereinbefore defined, for example at -20° C. in the presence of sulphuric acid and an appropriate organic solvent (e.g. methanol). Compounds of formula XXXII may be prepared by reacting a corresponding acid halide with diazomethane, for example at 20° C. in the presence of a suitable organic solvent (e.g. diethyl ether).

(i) Compounds of formula XVI in which $R_x$ represents a structural fragment of formula IIa, in which $X^1$ includes $N(R^{25})$, or IIc, in which $X_4$ represent $N(R^{23})$, (as appropriate), and $R^{23}$ and $R^{25}$ (as appropriate) represent $C_{1-4}$ alkyl, may be prepared by reaction of a corresponding compound of formula XVI in which $X_1$ includes, or $X_4$ represents, (as appropriate) NH with a compound of formula XXXIII $$R^a-Hal \qquad \text{XXXIII}$$

wherein $R^a$ represents $C_{1-4}$ alkyl and Hal is as hereinbefore define, for example under conditions which are well known to those skilled in the art.

(j) Compounds of formula XVI in which $R_x$ represents a structural fragment of formula IIa, in which the dotted lines represent bonds, A and E both represent CH and D represents —CH=CH—; $X_1$ represents —C(O)—N(H)—CH$_2$—; and $R^3$ is absent, may be prepared by catalytic hydrogenation of an hydroxamic acid of formula XXXIV,

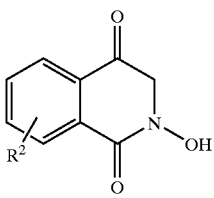

XXXIV wherein $R^2$ is as hereinbefore defined, using an appropriate catalyst system (e.g. Pd/C) in the presence of a suitable organic solvent (e.g. methanol). Compounds of formula XXXIV may be prepared by cyclisation of a corresponding compound of formula XXXV,

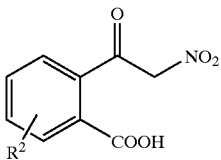

XXXV wherein $R^2$ is as hereinbefore defined, for example at 20° C. in the presence of fuming HCl and tin dichloride.

(k) Selective oxidation of a compound of formula XXXVI, $$H-R_x-H \qquad \text{XXXVI}$$

wherein $R_x$ is as hereinbefore defined, for example in the presence of a suitable oxidising agent (e.g. CrO$_3$ or KMnO$_4$) and an appropriate solvent (e.g. water).

(l) Selective oxidation of a compound of formula XXXVII, $$H-R_x-OH \qquad \text{XXXVII}$$

wherein $R_x$ is as hereinbefore defined, for example in the presence of a suitable oxidising agent (e.g. MnO$_2$) in an appropriate organic solvent (e.g. CH$_2$Cl$_2$).

(m) Hydrolysis of an oxime formula XXXVIII, $$R_x=N-OH \qquad \text{XXXVIII}$$

wherein $R_x$ is as hereinbefore define, for example by heating in the presence of acid (e.g. HCl) and an appropriate organic solvent. Compounds of formula XXXVIII may be prepared by reaction of a corresponding compound of formula XXXVI, as hereinbefore defined, with propyl nitrite, for example in the presence of HCl in ethanol.

(n) Compounds of formula XVI in which $R_x$ represents a structural fragment of formula IIa and $X^1$ represents —CH$_2$—CH=CH—, may be prepared by elimination of a compound of formula XXXIX,

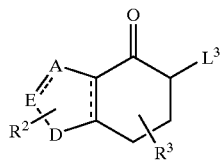

XXXIX wherein $L^3$ represents a suitable leaving group (e.g. Br or SePh) and the dotted lines, A, E, D, $R^2$ and $R^3$ are as hereinbefore define, under appropriate reaction conditions, for example in the presence of aqueous ethanolic NaOH or hydrogen peroxide, and an appropriate organic solvent (e.g. THF).

(o) Compounds of formula XVI in which $R_x$ represents a structural fragment of formula IIb, $X_2$ represents —C(O)—A$^4$— and A$^4$ is as hereinbefore define, may be prepared by cyclisation of a compound of formula XL,

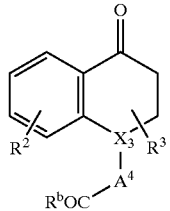

XL wherein $R^b$ represents OH, $C_{1-6}$ alkoxy or Hal and $R^2$, $R^3$, A$^4$, $X_3$ and Hal are as hereinbefore defined, for example in the presence of polyphosphoric acid, as described hereinbefore or, in the case where $R^b$ represents Hal, in the presence of AlCl$_3$ in nitromethane at, for example, 20° C.

(p) Compounds of formula XVI in which $R_x$ represents a structural fragment of formula IIb and $X_2$ represents —A$^4$—C(O)— and A$^4$ represents $C_{1-2}$ alkylene may be prepared by cyclisation of a compound of formula XLI,

XLI

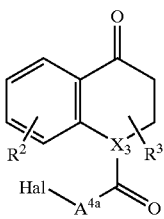

wherein $A^{4a}$ represents $C_{1-2}$ alkylene and Hal, $R^2$, $R^3$ and $X_3$ are as hereinbefore define.

Compounds of formulae VII, IX, X, XI, XII, XIII, XV, XVIA, XVII, XVIII, XXI, XXII, XXIII, XXIV, XXV, XXVI, XXVII, XXX, XXXI, XXXIII, XXXV, XXXVI, XXXVII, XXXIX, XL and XLI, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

Substituents on the aromatic and/or non-aromatic, carbocyclic and/or heterocyclic ring(s) in compounds of formulae I, IV, V, VI, VII, VIII, IX, X, XI, XIII, XVI, XVIA, MX, XX, XII, XXII, XXIII, XXVI, XXIX, XXX, XXX, XXXII, XXXV, XXXV, XXXVI, XXXVII, XXXVIII, XXXX, XL and XLI may be introduced and/or interconverted using techniques well known to those skilled in the art. For example, nitro may be reduced to amino, hydroxy may be alkylated to give alkoxy, alkoxy may be hydrolysed to hydroxy, alkenes may be hydrogenated to alkanes, halo may be hydrogenated to H, etc.

The compounds of formula I may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino, amidino and guanidino include t-butyloxycarbonyl, benzyloxycarbonyl or 2-trimethylsilylethoxycarbonyl (Teoc). Amidino and guanidino nitrogens may also be protected by hydroxy or alkoxy groups, and may be either mono- or diprotected.

The protection and deprotection of functional groups may take place before or after coupling, or before or after any other reaction in the abovementioned schemes.

Protecting groups may be removed in accordance with techniques which are well known to those skilled in the art and as described hereinafter.

Persons skilled in the art will appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

For example, this is particularly true in respect of the synthesis of compounds of formula I in which $D^1$ or $D^2$ (as appropriate) does not represent H, In this case, $OR^a$ and/or $C(=X^{11})X^{12}R^b$ groups may be introduced at an earlier stage in the overall synthesis using the process steps described hereinbefore.

Accordingly, the order and type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

The protected derivatives of compounds of formula I may be converted chemically to compounds of formula I using standard deprotection techniques (e.g. hydrogenation). The skilled person will appreciate that certain compounds of the invention may be regarded as protected derivatives of other compounds of the invention.

Medical and Pharmaceutical Use

Compounds of the invention may possess pharmacological activity as such. Compounds of the invention that may possess such activity include, but are not limited to, those with a free amidine functionality as part of the structural fragment B.

However, other compounds of formula I (including those that do not possess such a free amidine functionality) may not possess such activity, but may be administered parenterally or orally, and thereafter metabolised in the body to form compounds that are pharmacologically active (including, but not limited to, corresponding free amidine compounds). Such compounds (which also include compounds that may possess some pharmacological activity, but that activity is appreciably lower than that of the active compounds to which they are metabolised to), may therefore be described as "prodrugs" of the active compounds.

Thus, the compounds of the invention are useful because they possess pharmacological activity, and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, the compounds of the invention are potent inhibitors of thrombin either as such and/or (e.g. in the case of prodrugs), are metabolised following administration to form potent inhibitors of thrombin, for example as demonstrated in the tests described below.

By "prodrug of a thrombin inhibitor", we include compounds that form a thrombin inhibitor, in an experimentally-detectable amount, and within a predetermined time (e.g. about 1 hour), following oral or parenteral administration.

The compounds of the invention are thus expected to be useful in those conditions where inhibition of thrombin is required.

The compounds of the invention are thus indicated in the treatment and/or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of reocclusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may be, or may be metabolised to compounds that may be, more efficacious, be less toxic, be longer acting, have a broader range of activity, be more potent, produce fewer side effects, be more easily absorbed than, or that they may have other useful pharmacological, physical, or chemical, properties over, compounds known in the prior art.

Biological Tests

Test A

Determination of Thrombin Clotting Time (TT)

The inhibitor solution (25 μL) was incubated with plasma (25 μL) for three minutes. Human thrombin (T 6769; Sigma Chem. Co) in buffer solution, pH 7.4 (25 μL) was then added and the clotting time measured in an automatic device (KC 10; Amelung).

The clotting time in seconds was plotted against the inhibitor concentration, and the $IC_{50}TT$ was determined by interpolation.

$IC_{50}TT$ is the concentration of inhibitor in the test that doubles the thrombin clotting time for human plasma.

Test B

Determinaton of Thrombin Inhibition with a Chromogenic, Robotic Assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 1 mmol/L, were diluted serially 1:3 (24+48 μL) with DMSO to obtain ten different concentrations, which were analysed as samples in the assay. 2 μL of test sample was diluted with 124 μL assay buffer, 12 μL of chromogenic substrate solution (S-2366, Chromogenix, Möndal, Sweden) in assay buffer and finally 12 μL of a-thrombin solution, (Human α-thrombin, Sigma Chemical Co.) both in assay buffer, were added, and the samples mixed. The final assay concentrations were: test substance 0.00068–13.3 μmol/L, S-2366 0.30 mmol/L, α-thrombin 0.020 NIHU/mL. The linear absorbance increment during 40 minutes incubation at 37° C. was used for calculation of percentage inhibition for the test samples, as compared to blanks without inhibitor. The $IC_{50}$-robotic value, corresponding to the inhibitor concentration which caused 50% inhibition of the thrombin activity, was calculated from a log concentration vs. % inhibition curve.

Test C
Determinaton of the Inhibition Constant $K_i$ for Human Thrombin $K_i$-determinations were made using a chromogenic substrate method, performed at 37° C. on a Cobas Bio centrifugal analyser (Roche, Basel, Switzerland). Residual enzyme activity after incubation of human α-thrombin with various concentrations of test compound was determined at three different substrate concentrations, and was measured as the change in optical absorbance at 405 nm.

Test compound solutions (100 μL; normally in buffer or saline containing BSA 10 g/L) were mixed with 200 μL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, was added to 320 μL of the substrate S-2238 (Chromogenix AB, Mölndal, Sweden) in assay buffer, and the absorbance change (ΔA/min) was monitored. The final concentrations of S-2238 were 16, 24 and 50 μmol/L and of thrombin 0.125 NIH U/mL.

The steady state reaction rate was used to construct Dixon plots, i.e. diagrams of inhibitor concentration vs. 1/(ΔA/min). For reversible, competitive inhibitors, the data points for the different substrate concentrations typically form straight lines which intercept at $x=-K_i$.

Test D
Determination of Activated Partial Thromboplastin Time (APTT)

APTT was determined in pooled normal human citrated plasma with the reagent PTT Automated 5 manufactured by Stago. The inhibitors were added to the plasma (10 μL inhibitor solution to 90 μL plasma) and incubated with the APTT reagent for 3 minutes followed by the addition of 100 μL of calcium chloride solution (0.025M) and APTT was determined in the mixture by use of the coagulation analyser KC10 (Amelung) according to the instructions of the reagent producer. The clotting time in seconds was plotted against the inhibitor concentration in plasma and the $IC_{50}$APTT was determined by interpolation.

$IC_{50}$APTT is defined as the concentration of inhibitor in human plasma that doubled the Activated Partial Thromboplastin Time.

Test E
Determination of Thrombin Time ex vivo

The inhibition of thrombin after oral or parenteral administration of the compounds of formula I, dissolved in ethanol:Solutol™:water (5:5:90), were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L) and 9 parts of blood. The tubes were centrifuged to obtain platelet poor plasma. The plasma was used for determination of thrombin time as described below.

The citrated rat plasma, 100 μL, was diluted with a saline solution, 0.9%, 100 μL, and plasma coagulation was started by the addition of human thrombin (T 6769, Sigma Chem Co, USA) in a buffer solution, pH 7.4, 100 μL. The clotting time was measured in an automatic device (KC 10, Amelumg, Germany).

Where a "prodrug" compound of formula I was administered, concentrations of the appropriate active thrombin inhibitor of formula I (e.g. the free amidine or guanidine compound) in the rat plasma were estimated by the use of standard curves relating the thrombin time in the pooled citrated rat plasma to known concentrations of the corresponding "active" thrombin inhibitor dissolved in saline.

Based on the estimated plasma concentrations of the active thrombin inhibitor (which assumes that thrombin time prolongation is caused by the aforementioned compound) in the rat, the area under the curve after oral and/or parenteral administration of the corresponding prodrug compound of formula I was calculated (AUCpd) using the trapezoidal rule and extrapolation of data to infinity.

The bioavailability of the active thrombin inhibitor after oral or parenteral administration of the prodrug was calculated as below:

[(AUCpd/dose)/(AUCactive,parenteral/dose)]×100 where AUCactive,parenteral represents the AUC obtained after parenteral administration of the corresponding active thrombin inhibitor to conscious rats as described above.

Test F
Determination of Thrombin Time in Urine ex vivo

The amount of the "active" thrombin inhibitor that was excreted in urine after oral or parenteral administration of "prodrug" compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem Company) in buffer solution (pH 7.4; 100 μL). The clotting time was measured in an automatic device (KC 10; Amelung).

The concentrations of the active thrombin inhibitor in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor after oral or parenteral administration of the prodrug was calculated as below:

[(AMOUNTpd/dose)/(AMOUNTactive,parenteral/dose)]×100 where AMOUNTactive,parenteral represents the amount excreted in the urine after parenteral administration of the corresponding active thrombin inhibitor to conscious rats as described above.

Test G
Metabolic Activation of Prodrug Compounds in vitro

Prodrug compounds of formula I were incubated at 37° C. with liver microsomes or 10 000 g (referring to the centrifuge speed) supernatant fractions (i.e. s9 fraction) prepared from human or rat liver homogenate. The total protein concentration in the incubations were 1 or 3 mg/mL dissolved in 0.05 mol/L TRIS buffer (pH 7.4), and with the cofactors NADH (2.5 mmol/L) and NADPH (0.8 mmol/L) present. The total volume of the incubate was 1.2 mL. The initial prodrug concentrations were 5 or 10 μmol/L. Samples were collected from the incubate at regular intervals more than 60 minutes after the start of the incubations. Samples (25 μL) from the incubate were mixed with an equal volume of human or rat plasma and an appropriate amount of thrombin, and the clotting time (i.e. thrombin time) was measured on a coagulometer (KC 10; Amelumg). The amount of "active" thrombin inhibitor formed was estimated by the use of standard curves relating the thrombin time in pooled citrated human or rat plasma to known concentrations of the corresponding "active thrombin inhibitor".

EXAMPLES

The invention is illustrated by way of the following examples. The amino acids Pro and Aze are defined as the S-isomers if not otherwise specified. The examples were obtained as diastereoisomers if not otherwise specified.

Example 1

(S) or (R)-1-Hydroxy-7-methoxytetralin-1-yl-C(O)-Aze-Pab(CO—O—CH$_2$-cyclopropyl)

(i) 1-Hydroxy-7-methoxytetralin-1-yl-carboxylic acid, methyl ester

The sub-title compound was prepared according to the method described by C. F. Bigge et al in J. Med. Chem., (1993), 36, 1977 using 7-methoxytetralone (1.0 g; 5.67 mmol) and methanol instead of ethanol. Yield: 1.22 g (90%).

$^1$H-NMR (300 MHz; CDCl$_3$): δ7.05 (d, 1H), 6.80 (d, 1H), 6.65 (s, 1H), 3.80 (s, 3H), 3.75 (s, 3H), 2.85–2.65 (m, 2H), 2.25–1.90 (m, 4H)

(ii) 1-Hydroxy-7-methoxytetralin-1-yl-carboxylic acid

LiOH.H$_2$O (0.41 g; 9.8 mmol) and water (4 mL) were added to a solution of 1-hydroxy-7-methoxytetralin-1-yl-carboxylic acid, methyl ester (1.16 g; 4.9 mmol; from step (i) above) in THF (10 mL). The reaction mixture was stirred at room temperature for 3 h, the THF was evaporated, and the water phase was washed with methylene chloride. The reaction mixture was acidified with HCl (2M) and some NaCl was added. After extraction with methylene chloride, the organic phase was dried and concentrated. Yield: 765 mg (70%).

$^1$H-NMR (400 MHz; CDCl$_3$): δ7.07 (d, 1H), 6.82 (dd, 1H), 6.77 (d, 1H), 3.76 (s, 3H), 2.83–2.71 (m, 2H), 2.32–2.21 (m, 1H), 2.12–1.88 (m, 3H)

LC-MS (m/z) 221 (M−1)$^-$ (iii) (S)- and (R)-1-Hydroxy-7-methoxytetraline-1-yl-C(O)-Aze-Pab(Z)

TBTU (0.584 g; 1.7 mmol) and DIPEA (0.200 g; 1.55 mmol) were added, in that order, to an ice-cold solution of 1-hydroxy-7-methoxytetraline-1-yl-carboxylic acid (0.345 g; 1.55 mmol, from step (ii) above) in DMF (10 mL). After stirring at 0° C. for 15 minutes, H-Aze-Pab(Z) x 2HCl (0.750 g; 1.7 mmol; see international patent application WO 97/02284) and DIPEA (0.603 g; 4.65 mmol) were added and the mixture was stirred at RT for 4 days. The DMF was evaporated, and the resulting material was partitioned between water and EtOAc. The organic layer was separated, the water phase was extracted 3 times with EtOAc, and the combined organic layer was dried (Na$_2$SO$_4$) and concentrated. The product, a white powder, was further purified using HPLC (CH$_3$CN:0.1M ammonium acetate; 46:54), yielding 122 mg (28%) of a faster moving fraction (Compound 1A) and 63 mg (14%) of a slower moving fraction (Compound 1B).

Compound 1A:

$^1$H-NMR (400 MHz; CDCl$_3$): (complex due to diastereomers/rotamers) δ8.22 (t, 0.5H, rotamer); 7.94 (t, 0.5H, rotamer); 7.83 (t, 1H); 7.45–7.3 (m, 9H); 7.4 (t, 1H); 6.80 (m, 1H); 4.93 (m, 1H); 4.55 (m, 5H); 3.76 (s, 3H); 3.07–2.94 (m, 2H); 2.81 (m, 2H); 2.60 (m, 2H); 2.50 (m, 1H); 2.38 (m, 1H); 2.25 (m, 1H); 2.0–1.8 (m, 9H)

LC-MS (m/z) 571 (M+1)$^+$ (iv) (S)- or (R)-1-Hydroxy-7-methoxytetraline-1-yl-C(O)-Aze-Pab x HOAc Pd/C (5%; 50 mg) was added to a solution of (S) or (R)-1-hydroxy-7-methoxytetralin-1-yl-C(O)-Aze-Pab(Z) (58 mg; 0.01 mmol; Compound 1A from step (iii) above) in EtOH (5 mL) and HOAc (5.8 μL; 0.1 mmol), and the mixture was hydrogenated for 3 hours at room temperature and atmospheric pressure. The resulting mixture was filtered through Celite, the solution was concentrated, water was added and the solution was freeze dried, yielding 10 mg (98%) of the title compound. Yield 15 mg (59%).

$^1$H-NMR (400 MHz; D$_2$O): δ7.65 (d, 2H); 7.47 (d, 2H); 7.16 (d, 1H); 6.90 (d, 1H); 6.71 (d, 1H); 4.91 (dd, 1H); 4.40 (m, 1H); 4.15 (m, 1H); 3.94 (m, 1H); 3.60 (s, 3H); 2.75 (m, 3H); 2.53 (m, 1H); 2.1 (m, 2H); 2.0–1.75 (m, 7H)

$^{13}$C-NMR (100 MHz; CDCl$_3$) δ182.5; 178.3; 174.0

LC-MS (m/z) 437 (M+1)$^+$ (v) p-Nitrophenyl-cyclopropylmethyl carbonate

Pyridine (0.43 g; 5.5 mmol) was added to an ice-cold solution of cyclopropylmethanol (0.36 g; 5.0 mmol) and p-nitrophenyl chloroformate (1.06 g; 5.3 mmol) in methylene chloride (10 mL), and the resultant mixture was stirred at RT overnight, whereafter the solution was washed with KHSO$_4$ (3×) and brine, dried (Na$_2$SO$_4$), and concentrated, yielding 1.2 g (97%) of the sub-title compound.

$^1$H-NMR (400 MHz; CDCl$_3$): δ8.29 (m, 2H); 7.41 (m, 2H); 4.14 (d, 2H); 1.35–1.2 (m, 1H); 0.69 (m, 2H); 0.41 (m, 2H)

(vi) (S) or (R)-1-Hydroxy-7-methoxytetralin-1-yl-C(O)-Aze-Pab(CO—O—CH$_2$-cyclopropyl)

NaOH (aq; 1.5M; 1.2 mL; 1.8 mmol) was added to a vigorously stirred solution of (S)- or (R)-1-hydroxy-7-methoxytetralin-1-yl-C(O)-Aze-Pab x HOAc (40 mg; 80 μmol; from step (iv) above) and p-nitrophenyl-cyclopropylmethyl carbonate (17 mg; 71 μmol; from step (v) above) in methylene chloride (5 mL) and the solution was stirred at RT for 2 hours, whereafter the organic layer was washed 3 times with NaOH (aq, 1.5M). The crude product was purified using flash chromatography (silica gel; methylene chloride→EtOAc). The fractions of interest were concentrated, dissolved in water and freeze dried, yielding 33 mg (77%) of the title compound.

$^1$H-NMR (400 MHz; CDCl$_3$): δ7.96 (t, 1H); 7.85 (d, 2H); 7.31 (d, 2H); 7.05 (d, 1H); 6.83 (dd, 1H); 6.66 (d, 1H); 4.92

(dd, 1H); 4.6–4.4 (m, 3H); 3.99 (d, 2H); 3.83 (m, 1H); 3.75 (s, 3H); 3.04 (m, 1H); 2.80 (m, 1H); 2.5–2.7 (m, 2H); 2.25 (m, 1H); 1.8–1.2 (m, 4H); 1.24 (m, 1H); 0.59 (m, 2H); 0.33 (m, 2H)

$^{13}$C-NMR (100 MHz; CDCl$_3$): (carbonyl and/or amidine carbons): δ178.8; 171.4; 168.6; 165.0.

LC-MS (m/z) 536 (M+1)$^+$

Example 2

(S)- or (R)-1-Hydroxy-7-methoxytetralin-1-yl-C(O)-Aze-Pab(CO—O-cyclopentyl)

NaOH (aq; 1.5M; 0.44 mL; 0.66 mmol) was added to a solution of (S)- or (R)-1-hydroxy-7-methoxytetralin-1-yl-C(O)-Aze-Pab x HOAc (30 mg; 60 μmol; see Example 1(iv) above) and cyclopentyl chloroformate (9.9 mg; 66 μmol) in methylene chloride, and the mixture was stirred at RT for 3 hours, whereafter it was diluted with water, and the resultant mixture was extracted with methylene chloride (4×). The combined organic layer was dried (Na$_2$SO$_4$) and evaporated. The crude product was purified using flash chromatography (silica gel; methylene chloride→EtOAc). The fractions of interest were concentrated, yielding 16.7 mg (50%) of the title compound.

$^1$H-NMR (400 MHz; CDCl$_3$): δ7.95 (t, 1H); 7.83 (d, 2H); 7.32 (d, 2H); 7.06 (d, 1H); 6.83 (dd, 1H); 6.67 (d, 1H); 5.16 (m, 1H); 4.93 (dd, 1H); 4.6–4.45 (m, 3H); 3.84 (m, 1H); 3.77 (s, 3H); 3.04 (m, 1H); 2.82 (m, 1H); 2.7–2.55 (m, 2H); 2.26 (m, 1H); 2.0–1.7 (m, 10H); 1.65–1.55 (m, 2H)

$^{13}$C-NMR (100 MHz; CDCl$_3$): (carbonyl and/or amidine carbons): δ178.8; 171.4; 168.5; 165.9

LC-MS (m/z) 549 (M+1)$^+$

Example 3

(S)- or (R)-1-Hydroxy-7-methoxytetralin-1-yl-C(O)-Aze-Pab(CO—O-cyclobutyl)

(i) p-Nitrophenyl-cyclobutyl carbonate

Pyridine (0.43 g; 5.5 mmol) was added to an ice-cold solution of cyclobutanol (0.36 g; 5.0 mmol) and p-nitrophenyl chloroformate (1.0 g; 5.0 mmol) in methylene chloride (10 mL), and the resultant mixture was stirred at RT overnight. The crude product was purified using flash chromatography (silica gel; heptane→heptane:EtOAc (90:10)). The fractions of interest were concentrated yielding 0.86 g (73%) of the sub-title compound.

$^1$H-NMR (400 MHz; CDCl$_3$): δ8.29 (m, 2H); 7.39 (m, 2H); 5.07 (m, 1H); 2.45 (m, 2H); 2.25 (m, 2H); 1.89 (m, 1H); 1.68 (m, 1H)

(ii) (S)- or (R)-1-Hydroxy-7-methoxytetralin-1-yl-C(O)-Aze-Pab(CO—O-cyclobutyl)

NaOH (aq; 1.5M; 1 mL; 1.5 mmol) was added to a vigorously stirred solution of (S)- or (R)-1-hydroxy-7-methoxytetralin-1-yl-C(O)-Aze-Pab x HOAc (30 mg; 60 μmol; see Example 1(iv) above) and p-nitropbenyl-cyclobutyl carbonate (36 mg; 150 μmol; from step (i) above) in methylene chloride (5 mL), whereafter the solution was stirred at RT for 2.5 hours. The resultant mixture was washed 3 times with NaOH (aq; 1.5M) and 2 times with brine. The crude product was purified using flash chromatography (silica gel; methylene chloride:EtOAc (3:10)). The fractions of interest were concentrated yielding 24 mg (74%) of the title compound.

$^1$H-NMR (400 MHz; CDCl$_3$): δ9.6 (br, 1H); 7.96 (t, 1H); 7.84 (d, 2H); 7.31 (d, 2H); 7.05 (d, 1H); 6.82 (dd, 1H); 6.67 (d, 1H); 5.00 (p, 1H); 4.92 (dd, 1H); 4.54 (br, 1H); 4.50 (m, 1H); 3.83 (m, 1H); 3.04 (m, 1H); 2.81 (d, 1H); 2.65–2.5 (m, 2H); 2.45–2.3 (m, 2H); 2.3–2.15 (m, 3H); 2.0–1.8 (m, 5H); 1.64 (m, 1H)

$^{13}$C-NMR (100 MHz; CDCl$_3$): (carbonyl and/or amidine carbons): δ178.8; 171.4; 168.7; 165.3

LC-MS (m/z) 536 (M+1)$^+$

Example 4

(R,S)-4-Hydroxy-6-chlorochroman-4-yl-C(O)-Aze-Pab(CO—O—CH$_2$-cyclopropyl)

(i) 6-Chloro-4-hydroxychroman-4-yl-carboxylic acid

The sub-title compound was prepared analogously to the methods described in Example 1, steps (i) and (ii), starting from 6-chlorochromanone (2.45 g; 13.4 mmol), Me$_3$SiCN (1.51 g; 15.2 mmol), and ZnI$_2$ (40 mg; cat.). Yield: 490 mg (93%).

LC-MS (m/z) 228 (M−1)$^−$ (ii) Boc-Aze-Pab x HCOOH

Ammonium formate (3.0 g; 50 mmol) and Pd/C (5%; 1.0 g) were added to a solution of Boc-Aze-Pab(Z) (4.7 g; 10 mmol; see international patent application WO 94/29336) in 50 mL of MeOH. Formic acid (1.0 g; 22 mmol) was added and the mixture was stirred for 30 minutes. The reaction mixture was filtered through Hyflo and the solution was concentrated. The crude product was suspended in CH$_2$Cl$_2$ (50 mL), filtered and washed with more CH$_2$Cl$_2$. The solid material was dried and used in the following step without further purification.

(iii) Boc-Aze-Pab(Teoc)

Teoc-p-nitrophenyl carbonate (3.5 g; 12.3 mmol) was added to a solution of Boc-Aze-Pab x HCOOH (3.7 g; 10 mmol; from step (ii) above) in THF (100 mL) whereafter a solution of K$_2$CO$_3$ (1.8 g; 13 mmol) in water (20 mL) was added over 2 minutes. The resultant solution was stirred for 3 days, concentrated, and the remainder was taken up in EtOAc (150 mL) and NaOH (aq.; 0.5M; 50 mL). The organic layer was washed with brine (2×50 mL), dried (Na$_2$SO$_4$) and concentrated. The crude product was purified using flash chromatography (Si-gel; methylene chloride:acetone; 4:1). Yield 4.6 g (96%).

$^1$H-NMR (500 MHz; CDCl$_3$): δ7.86 (d, 2H); 7.39 (d, 2H); 4.72 (bt, 1H); 4.7–4.5 (br, 2H); 3.93 (m, 1H); 3.81 (m, 1H); 2.48 (br, 2H); 1.43 (s, 9H); 0.09 (s, 9H)

(iv) H-Aze-Pab(Teoc) x HCl

A solution of Boc-Aze-Pab(Teoc) (4.6 g; 9.6 mmol; from step (iii) above) in methylene chloride (150 mL) was saturated with dry HCl. The solution was kept at RT in a stoppered flask for 10 minutes, whereafter it was concentrated. Yield 4.2 g (97%).

$^1$H-NMR (400 MHz; CD$_3$OD): δ7.80 (d, 2H); 7.60 (d, 2H); 5.10 (m, 1H); 4.60 (bs, 2H); 4.15 (m, 1H); 3.97 (q, 1H); 2.86 (m, 1H); 2.57 (m, 1H); 0.11 (s, 9H)

(v) 6-Chloro-4-hydroxychroman-4-yl-C(O)-Aze-Pab (Teoc)

A solution of 6-chloro-4-hydroxychroman-4-yl-carboxylic acid (222 mg; 1.00 mmol; from step (i) above)

and HATU (370 mg, 0.97 mmol) in DMF (5 mL) was stirred at 0° C. for 1.5 h, and a mixture of H-Aze-Pab(Teoc) x HCl (440 mg, 0.98 mmol; from step (iv) above) and 2,4,6-trimethylpyridine (0.48 g; 3.9 mmol) in DMF (5 mL) was added at 0° C. After stirring 3 h at 0° C. the reaction mixture was concentrated, and the crude product was purified using preparative RPLC (CH$_3$CN:0.1M ammonium acetate; 55:45). The fractions of interest were partly concentrated and extracted with methylene chloride. The organic layer was dried (Na$_2$SO$_4$) and concentrated, yielding 350 mg (67%) of a diastereomeric mixture.

$^1$H-NMR (400 MHz; CDCl$_3$) (complex due to diastereomers/rotamers): δ7.96 (m, 0.5H); 7.87 (bd, 1H); 7.82 (bd, 1H); 7.73 (m, 0.5H); 7.31 (m, 1H); 7.19 (dt, 1H); 7.09 (bd, 0.5H); 7.00 (bd, 0.5H); 6.88 (dd, 1H); 4.93 (m, 1H); 4.9–4.4 (m, 4H); 4.36 (m, 1H); 4.15 (bt, 1H); 3.89 (m, 0.5H); 3.74 (m, 0.5H); 3.09 (m, 1H); 2.65–2.25 (m, 4H); 1.96 (bt, 1H); 0.06 (s, 9H)

LC-MS (m/z) 588 (M+1)$^+$ $^{13}$C-NMR (100 MHz; CDCl$_3$): (carbonyl and/or amidine carbons) δ176.9; 171.5; 171.3; 169.8; 155.4; 155.2

(vi) (R,S)-6-Chloro-4-hydroxychroman-4yl-C(O)-Aze-Pab x HOAc

Bu$_4$NF (1.0M in THF; 0.35 mL) was added to a solution of 6-chloro-4-hydroxychroman-4-yl-C(O)-Aze-Pab(Teoc) (190 mg; 0.32 mmol; from step (v) above) in THF (20 mL) at 0° C. The solution was stirred for two days at 40° C. The solution was concentrated and the crude material was purified using preparative RPLC (CH$_3$CN:0.1M ammonium acetate; 25:75). Yield 115 mg (71%).

$^1$H-NMR (400 MHz; CD$_3$OD): δ7.73 (m, 2H); 7.55 (m, 2H); 7.28 (dd, 1H); 7.15 (m, 1H); 6.79 (m, 1H); 4.7–4.0 (m, 6H); 2.8–2.0 (m, 4H); 1.90 (s, 3H)

LC-MS (m/z) 444 (M+1)$^+$ $^{13}$C-NMR (100 MHz; CDCl$_3$): (carbonyl and/or amidine carbons) δ175.9; 175.6, 174.4; 173.1; 173.0

(vii) (R,S)-4-Hydroxy-6-chlorochroman-4-yl-C(O)-Aze-Pab(CO—O—CH$_2$-cyclopropyl)

NaOH (aq; 2M; 1.0 mL; 2.0 mmol) was added to a vigorously stirred solution of (R,S)-6-chloro-4-hydroxychroman-4-yl-C(O)-Aze-Pab x HOAc (31 mg; 62 μmol; from step (vi) above) and p-nitrophenyl-cyclopropylmethyl carbonate (39 mg, 160 μmol, see Example 1(v) above) in methylene chloride (5 mL), and the solution was stirred at RT for 2 hours. The resultant mixture was washed 3 times with NaOH (aq.; 1.5M). The crude product was purified using flash chromatography (silica gel; methylene chloride→EtOAc). The fractions of interest were concentrated yielding 25 mg (75%) of the title compound.

$^1$H-NMR (400 MHz; CDCl$_3$): (complex due to diastereoisomers) δ7.95 (t, 0.5H); 7.85 (d, 1H); 7.80 (m, 1.5H); 7.33 (d, 1H); 7.27 (d, 1H); 7.17 (m, 2H); 7.08 (d, 0.5H); 6.82 (m, 1H); 4.90 (m, 1H); 4.6–4.4 (m, 3H); 4.14 (m, 1H); 3.96 (d, 2H); 3.90 (m, 0.5H); 3.75 (m, 0.5H); 3.11 (m, 1H); 2.51 (m, 1H); 2.40 (m, 0.5H); 2.30 (m, 0.5H); 2.22 (m, 1H); 1.95 (m, 1H); 0.56 (m, 2H); 0.31 (m, 2H)

$^{13}$C-NMR (100 MHz; CDCl$_3$): (carbonyl and/or amidine carbons) δ175.2; 175.1; 171.1; 170.0; 169.9; 167.5

LC-MS (m/z) 541 (M+1)$^+$

Example 5

(R)-1-Hydroxy-7-methoxytetralin-1-yl-C(O)-Aze-Pab(O—CH$_2$—Ph(4-OMe))

(i) (R)-1-hydroxy-7-methoxytetralin-1-yl-C(O)-Aze-Pab(Teoc)

The sub-title compound was prepared according to the method described in Example 4(v) above from 1-hydroxy-7-methoxytetraline-1-carboxylic acid (0.44 g; 2.0 mmol; see Example 1(ii) above), HATU (0.80 g; 2.1 mmol), H-Aze-Pab(Teoc) x HCl (1.17 g; 2.6 mmol; see Example 4(iv) above), and 2,4,6-trimethylpyridine (1.2 g; 10 mmol). The crude product (1.73 g) was purified using preparative RPLC (CH$_3$CN:0.1M ammonium acetate 55:45). The fractions of interest were partly concentrated and extracted with methylene chloride. The organic layer was dried (Na$_2$SO$_4$) and concentrated yielding 0.32 g (28%) of a diastereomeric mixture. Preparative RPLC (CH$_3$CN:0.1M ammonium acetate; 46:54) yielded two diastereomers: Compound 5A (faster moving diastereomer; 0.16 g; 28%) and Compound 5B (slower moving diastereomer; 0.16 g; 28%).

Compound 5A:

$^1$H-NMR (400 MHz; CDCl$_3$) δ7.96 (t, 1H); 7.86 (dd, 2H); 7.36 (dd, 2H); 7.07 (d, 1H); 6.87 (dd, 1H); 6.68 (d, 1H); 4.95 (dd, 1H); 4.54 (m, 3H); 4.26 (m, 2H); 3.84 (m, 1H); 3.78 (s, 3H); 3.04 (q, 1H); 2.83 (d, 1H); 2.63 (m, 2H); 2.28 (m, 1H); 2.02–1.85 (m, 4H); 1.15 (dt, 2H); 0.08 (s, 9H)

LC-MS (m/z) 581 (M+1)$^+$ (ii) (R)-1-Hydroxy-7-methoxytetralin-1-yl-C(O)-Aze-Pab(Teoc)(O—CH$_2$—Ph(4-OMe))

O-(4-methoxybenzyl)-hydroxylamine x HCl (78 mg; 0.41 mmol) was added to a solution of (R)-1-hydroxy-7-methoxytetralin-1-yl-C(O)-Aze-Pab(Teoc) (40 mg; 69 mmol; from step (i) above) in THF (3 mL), and the mixture was stirred at 60° C. overnight. The solution was concentrated, and the crude product was purified using preparative RPLC (65% CH$_3$CN/0.1M ammonium acetate). The fractions of interest were concentrated, and the remaining mixture was extracted with methylene chloride. The organic layer was washed with brine, dried (Na$_2$SO$_4$), and concentrated, yielding 35 mg (71%) of the sub-title compound.

$^1$H-NMR (400 MHz; CDCl$_3$): δ7.79 (bt, 1H); 7.55 (s, 1H); 7.45 (d, 2H); 7.34 (m, 2H); 7.28 (s, 2H); 7.04 (d, 1H); 6.91 (m, 2H); 6.82 (dd, 1H); 6.65 (d, 1H); 5.09 (s, 2H); 4.91 (dd, 1H); 4.65 (br, 1H); 4.49 (m, 2H); 4.11 (m, 2H); 3.83 (s, 3H); 3.76 (s, 3H); 2.95 (m, 1H); 2.80 (bd, 1H); 2.60 (m, 2H); 2.25 (m, 1H); 2.0–1.8 (m, 4H); 0.94 (m, 2H); 0.00 (s, 9H)

$^{13}$C-NMR (100 MHz; CDCl$_3$): (carbonyl and/or amidine carbons) δ177.3; 170.6; 161.3; 156.6

LC-MS (m/z) 717 (M+1)$^+$ (iii) (R)-1-Hydroxy-7-methoxytetralin-1-yl-C(O)-Aze-Pab(O—CH$_2$—Ph(4-OMe))

Bu$_4$NF (1M in THF; 0.1 mL; 0.1 mmol) was added to a solution of (R)-1-hydroxy-7-methoxytetralin-1-yl-C(O)-Aze-Pab(Teoc)(O—CH$_2$—Ph(4-OMe)) (34 mg; 44 mmol; from step (ii) above) in CH$_3$CN (2 mL) and the solution was stirred at 60° C. overnight. The crude product (21.3 mg) was purified using HPLC (65% CH$_3$CN/0.1M ammonium acetate, yielding 10 mg (46%) of the title compound.

$^1$H-NMR (400 MHz; CDCl$_3$) δ7.87 (br, 1H); 7.61 (d, 2H); 7.39 (d, 2H); 7.29 (d, 2H); 7.07 (d, 2H); 6.91 (d, 2H); 6.83 (dd, 1H); 6.67 (d, 1H); 5.07 (s, 2H); 4.93 (dd, 1H); 4.84 (br, 1H); 4.59 (br, 1H); 4.49 (m, 2H); 3.82 (s, 3H); 3.77 (s, 3H); 3.02 (m, 1H); 2.82 (bd, 1H); 2.68–2.55 (m, 2H); 2.26 (m, 1H); 2.0–1.8 (m, 5H)

$^{13}$C-NMR (100 MHz; CDCl$_3$): (carbonyl and/or amidine carbons) δ177.9; 170.4; 158.8

LC-MS (m/z) 573 (M+1)$^+$

Example 6

4-Hydroxy-6-chloro-8-trifluoromethoxychroman-4-yl-C(O)-Aze-Pab (i) O—CF$_3$—O'-allyl-catechol A solution of O—CF$_3$-catechol (10 g, 56.2 mmol) and allyl bromide (13.6 g, 112.3 mmol) and Cs$_2$CO$_3$ (36.6 g, 112.3 mmol) in acetone (100 mL) was refluxed overnight, and the solvent was removed using a rotary evaporator. The remainder was dissolved in ether, and the resultant mixture was washed with NaOH/H$_2$O (2M) and water. The product (10.9 g, 89%) was pure enough to use without further purification.

$^1$H NMR (400 MHz, CDCl$_3$) δ7.26 (m, 2H); 6.96 (m, 2H); 6.06 (m, 1H); 5.47 (d, 1H); 5.33 (d, 1H); 4.65 (s, 2H)

(ii) O—CF$_3$—O'-3-hydroxy-n-propyl-catechol

To a cold (ice-bath) solution of O—CF$_3$—O'-allyl-catechol (8.9 g, 40.8 mmol, from step (i) above) in dry THF (100 mL) under N$_2$ was added borane-dimethylsulphide complex (2M, 59 mL, 118.3 mmol). The temperature of the mixture was kept below 5° C. and, following addition, was stirred in an ice-bath for 2 h and at ambient temperature for 1 h. The mixture was cooled and water (45 mL) was added. The mixture was stirred for a few minutes and then NaOH/H$_2$O (3M, 40 mL) and H$_2$O$_2$ (35%, 12.5 mL) were added. The mixture was stirred at RT for 1 h, K$_2$CO$_3$ was added and the solution was stirred for another 5 minutes. The organic layer was separated, the THF was evaporated and ether was added. The ether solution was dried (Na$_2$SO$_4$) and evaporated, yielding 7.30 g (76%) of crude product, which was used without further purification.

$^1$H NMR (400 MHz, CDCl$_3$) δ7.26 (m, 2H); 7.03 (d, 1H); 6.96 (m, 1H); 4.20 (m, 2H); 3.90 (m, 2H); 2.10 (m, 2H)

(iii) 3-(2-OCF$_3$-phenoxy)propionic acid

To a solution of CrO$_3$ (11.3 g, 112.6 mmol) and H$_2$SO$_4$ (conc., 9.5 mL) in water:acetone (21:250) was added a solution of O—CF$_3$—O'-3-hydroxy-n-propyl-catechol (7.0 g, 29.6 mmol, from step (ii) above) in acetone (140 mL), and the resultant mixture was stirred at RT for 2 h. iso-Propanol was added to destroy the remaining CrO$_3$, the precipitate was removed by filtration, and the acetone was evaporated. The residue was dissolved in methylene chloride and water, the organic layer was separated, and the aqueous layer was extracted twice with methylene chloride. The combined organic layer was washed with water and extracted with NaOH/H$_2$O (2M) whereafter the aqueous phase was washed with methylene chloride, acidified (HCl) and extracted with ether. After evaporation of the combined ethereal phase, the product, a yellow solid, was obtained (yield 4.37 g (59%)).

$^1$H NMR (600 MHz, CDCl$_3$) δ7.21 (m, 2H); 6.99 (d, 1H); 6.94 (m, 1H); 4.28 (t, 2H); 2.87 (t, 2H)

(iv) 8-Trifluoromethoxychroman-4-one

To a cold solution of 3-(2OCF$_3$-phenoxy)propionic acid (4.56 g, 18.2 mmol; from step (iii) above) in methylene chloride was added PCl$_5$ (6.45 g; 31.0 mmol) in portions, and the resultant mixture was stirred at 0° C. for 1 h. To the cold solution was added AlCl$_3$ (7.29 g, 54.7 mmol) and the mixture was stirred at 0° C. for 1 h, and then at RT overnight. The mixture was cooled and water (50 mL) was added cautiously. After addition of further methylene chloride the organic layer was separated and the aqueous layer was extracted twice with methylene chloride. The combined organic layer was washed with water, dried (Na$_2$SO$_4$) and concentrated, yielding 4.10 g (97%) of the sub-title compound.

$^1$H NMR (600 MHz, CDCl$_3$): δ7.83 (d, 1H); 7.41 (d, 1H); 6.99 (t, 1H); 4.61 (t, 2H); 2.84 (t, 2H)

(v) 6-Chloro-8-trifluoromethoxychroman-4-one

To a solution of calcium hypochlorite (15.4 g, 72.4 mmol) in water:acetic acid (65:5) was added a solution of 8-trifluoromethoxychroman-4-one (4.2 g, 18.1 mmol; from step (iv) above) in acetonitrile (20 mL), whereafter the reaction mixture was stirred overnight. The mixture was diluted with water and extracted with ether (3 times) and EtOAc (once). The combined organic layer was washed with water, dried (Na$_2$SO$_4$) and evaporated, yielding 4.2 g (87%) of the sub-title compound.

$^1$H NMR (300 MHz, CDCl$_3$): δ7.83 (m, 1H); 7.43 (m, 1H); 4.64 (t, 2H); 2.90 (t, 2H)

(vi) 4-Cyano-4-OTMS-6-chloro-8-trifluoromethoxychroman

A solution of 6-chloro-8-trifluoromethoxychroman-4-one (2.0 g, 7.5 mmol, from step (v) above), TMSCN (0.8 g, 8.3 mmol) and ZnI$_2$ (cat.) in methylene chloride (50 mL) was stirred at RT for 2 days, whereafter the crude product was used directly for the next step.

$^1$H NMR (300 MHz, CDCl$_3$) δ7.50 (d, 1H); 7.28 (sh, 1H); 4.52–4.38 (m, 2H); 2.52–2.38 (m, 2H); 0.26 (s, 9H)

(vii) 4-Hydroxy-6-chloro-8-trifluoromethoxy-4-carbimidic acid, methyl ester

The product solution from the step (vi) above was added drop-wise to an ice cold saturated solution of HCl in MeOH, whereafter the resultant mixture was stirred overnight. The solvent was removed in vacuo, and the resultant material was used directly to the next step.

(viii) 4-Hydroxy-6-chloro-8-trifluoromethoxychroman-4-yl carboxylic acid, methyl ester The crude product from step (vii) above was dissolved in THF (100 mL), and H$_2$SO$_4$ (0.5M, 100 mL) was added, whereafter the mixture was left standing at RT for 3 days. The solution was partially concentrated and the aqueous solution was extracted with ether (3×). The combined organic phase was dried (Na$_2$SO$_4$) and concentrated. The crude product was used directly in the next step.

(ix) 4-Hydroxy-6-chloro-8-trifluoromethoxychroman-4-yl carboxylic acid

A solution of 4-hydroxy-6-chloro-8-trifluoromethoxychroman-4-yl carboxylic acid, methyl ester in iso-propanol (50 mL) was added to KOH/H$_2$O (20%, 60 mL) and the mixture was refluxed overnight. The resultant solution was partially concentrated, and the remainder was acidified with H$_2$SO$_4$ (10%). The very turbid mixture was extracted with ether (3×), and the combined organic phase was dried (Na$_2$SO$_4$) and concentrated. The crude product was purified via prep-HPLC (CH$_3$CN:0.1M ammonium acetate (30:60)). The fractions of interest were partly concentrated and extracted with ether. The combined organic layers were washed with water, dried (Na$_2$SO$_4$), and concentrated, yielding 0.24 g (10% over steps (vi)–(ix)).

$^1$H NMR (600 MHz, CDCl$_3$) δ7.18 (s, 1H); 7.11 (s, 1H); 4.51 (m, 1H); 4.27 (m, 1H); 2.47 (m, 1H); 2.15 (m, 1H)

(x) 4-Hydroxy-6-chloro-8-trifluoromethoxychroman-4-yl-C(O)-Aze-Pab(Teoc)

To a solution of 4-hydroxychloro-8-trifluoromethoxychroman-4-yl carboxylic acid (0.24 g, 0.77 mmol; from step (ix) above), was added H-Aze-Pab(Teoc) (0.38 g, 0.84 mmol, see Example 4(iv) above), PyBOP (0.44 g, 0.84 mmol) in DMF (7 mL), and DIPEA (0.40 g, 3.07 mmol). The resultant mixture was stirred overnight, poured into water and then extracted with EtOAc (3×). The combined organic layer was washed with water, dried (Na$_2$SO$_4$) and concentrated. The crude product was purified by flash chromatography (methylene chloride:THF (7:3)) to yield 0.22 g (43%) of the subtitle product as a diastereomeric mixture.

$^1$H NMR (600 MHz, CDCl$_3$) (complex due to diastereomers/rotamers) δ7.79 (d, 1H); 7.76 (d, 1H); 7.67 (t, 1H); 7.31 (d, 1H); 7.25 (d, 1H); 7.18 (s, 1H); 7.04 (d, 0.5H); 7.00 (d, 0.5H); 4.87 (m, 1H); 4.60–4.36 (m, 3H); 4.22–4.13 (m, 3H); 3.91 (m, 0.5H); 3.76 (m, 0.5H); 3.14 (m, 1H); 2.55–2.20 (m, 3H); 1.98 (m, 1H); 1.07 (m, 2H); 0.03 (s, 9H)

LC-MS (m/z) 671 (M+1)$^+$ (xi) 4-Hydroxy-6-chloro-8-trifluoromethoxychroman-4-yl-C(O)-Aze-Pab A solution of 4-hydroxy-6-chloro-8-trifluoromethoxychroman-4-yl-C(O)-Aze-Pab(Teoc) (106 mg, 0.16 mmol; from step (x) above) in TFA (2 mL) was left at RT for 30 min, whereafter the solution was concentrated in vacuo. The product was dissolved in a minimal amount of water and freeze dried overnight, yielding 100 mg (99%) of the title compound with a purity of 96%.

$^1$H NMR (400 MHz, CD$_3$OD) (complex due to diastereomers/rotamers) δ7.74 (m, 2H); 7.60–7.50 (m, 2H); 7.38 (d, 0.5H); 7.30 (d, 0.5H); 7.24 (m, 1H); 4.87 (sh, 1H); 4.65–4.40 (m, 4H); 4.35–4.00 (m, 2H); 2.75 (m, 0.5H); 2.60 (m, 1H); 2.42 (m, 1H); 2.37–2.05 (m, 2.5H)

LC-MS (m/z) 527 (M+1)$^+$ $^{13}$C NMR (carbonyl and/or amidine carbons; 100 MHz, CD$_3$OD): δ174.1; 173.7; 172.0; 171.9; 166.9

Example 7

4-Hydroxy-6-chloro-8-trifluoromethoxychroman-4-yl-C(O)-Aze-Pab(OMe)

(i) 4-Hydroxy-6-chloro-8-trifluoromethoxychroman-4-yl-C(O)-Aze-Pab(OMe)(Teoc)

A solution of 4-hydroxy-6-chloro-8-trifluoromethoxychroman-4-yl-C(O)-Aze-Pab(Teoc) (40 mg, 0.06 mmol; see Example 6(x) above) and O-methylhydroxylamine (30 mg, 0.36 mmol) in THF (5 mL) was heated at 65° C. for 2 days, whereafter the solvent was removed in vacuo and the crude product was purified by prep-HPLC (CH$_3$CN:0.1M ammonium acetate 50:50–70:30). The fractions of interest were partly concentrated and extracted with EtOAc. The combined organic phase was dried (Na$_2$SO$_4$) and concentrated to dryness, giving the sub-title compound (22 mg, 53%).

$^1$H NMR (600 MHz, CDCl$_3$) (complex due to diastereomers/rotamers) δ7.64 (bt, 0.5H); 7.57 (d, 1H); 7.52 (d, 1H); 7.48 (d, 1H); 7.43 (bt, 0.5H); 7.34 (d, 1H); 7.29 (d, 1H); 7.23 (s, 1H); 7.09 (d, 0.5H); 7.06 (d, 0.5H); 4.90 (m, 1H); 4.75 (b, 1H); 4.61–4.44 (m, 3H); 4.22–4.12 (m, 3H); 3.96 (s, 3H); 3.90 (m, 0.5H); 3.76 (m, 0.5H); 3.15 (q, 0.5H); 3.05 (m, 0.5H); 2.59 (m, 1H); 2.44 (m, 0.5H); 2.36 (m, 0.5H); 2.25 (m, 1H); 2.02 (dd, 1H); 1.67 (b, 1H); 0.97 (m, 1H); 0.02 (d, 9H)

(ii) 4-Hydroxy-6-chloro-8-trifluoromethoxychroman-4-yl-C(O)-Aze-Pab(OMe)

A solution of 4-hydroxychloro-8-trifluoromethoxychroman-4-yl-C(O)-Aze-Pab(OMe)(Teoc) (22 mg, 0.03 mmol, from step (i) above) in TFA (3.0 mL) was stirred for 15 minutes, whereafter the solution was concentrated. The crude product was dissolved in water, and the product was freeze dried, yielding 20 mg (95%) of the title compound.

$^1$H NMR (600 MHz, CD$_3$OD) (complex due to diastereomers/rotamers) δ7.63 (m, 2H); 7.53 (m, 2H); 7.36 (m, 0.5H); 7.28 (m, 0.5H); 7.22 (m, 1H); 4.82 (dd, 1H); 4.62–4.00 (m, 6H); 3.92 (s, 3H); 2.71 (m, 0.5H); 2.55 (m, 0.5H); 2.40 (m, 1H); 2.27 (m, 0.5H); 2.20 (m, 0.5H); 2.10 (m, 1H)

LC-MS (m/z) 557 (M+1)$^+$ $^{13}$C NMR (carbonyl and/or amidine carbons; 100 MHz, CD$_3$OD) δ173.9; 173.6; 171.8; 160.6

Example 8

(S)- or (R)-4-Hydroxy-6-chloro-8-difluoromethoxychroman-4-yl-C(O)-Aze-Pab x HOAc (i) O—CHF$_2$—O'-allyl-catechol To a solution of isopropanol (120 mL) and KOH/H$_2$O (30%, 120 mL) was added O-allyl-catechol (26 g, 173 mmol). The resultant mixture was warmed to 70° C., and a stream of chlorodifluoromethane was bubbled through the solution for 45 minutes. The mixture was stirred for 30 minutes at 70° C. and then at room temperature overnight. The mixture was diluted with water (1000 mL), and extracted with ether (3×). The combined organic phases were washed with NaOH/H$_2$O (2M) and water, then dried (Na$_2$SO$_4$) and concentrated, yielding 20.5 g (59%) of the sub-title compound, which was used without further purification.

$^1$H-NMR (400 MHz; CDCl$_3$): δ7.15(m, 2H); 6.93 (m, 2H); 6.30–6.80 (t, 1H); 5.95–6.10 (m, 1H); 5.25–5.45 (dd, 2H); 4.55–4.60 (d, 2H)

(ii) O—CHF$_2$—O'-3-hydroxy-n-propyl-catechol

To a cold (ice-bath) solution of O—CHF$_2$—O'-allyl-catechol (20.5 g, 102.4 mmol, from step (i) above) in dry THF (200 mL) under N$_2$ was added borane-dimethylsulphide complex (2M, 149 mL, 298 mmol). The temperature of the mixture was kept at 5° C. and, following addition, was stirred at this temperature for 2 h, and then at room temperature for 1 h. The mixture was cooled and water (111 mL) was added. The mixture was stirred for a few minutes and then NaOH/H$_2$O (3M, 102 mL) and H$_2$O$_2$ (35%, 31 mL) were added. The mixture was stirred (ice-bath) for a few minutes and then at room temperature for 1 h. K$_2$CO$_3$ (77 g, 557 mmol) was added and the mixture was stirred for a few minutes. The organic layer was separated, the THF was evaporated and ether was added. The ether solution was washed with water (3×), then dried (Na$_2$SO$_4$) and concentrated, yielding 16.2 g (72%) of the sub-title compound, which was used without further purification.

$^1$H-NMR (400 MHz; CDCl$_3$): δ7.10–7.17 (m, 2H); 6.86–6.98 (m, 2H); 6.32–6.71 (t, 1H); 4.11 (t, 2H); 3.81 (t, 2H); 2.86 (s, 1H); 2.1 (m, 2H)

(iii) 3-(2-OCHF$_2$-phenoxy)propionic acid

To a cold (ice-bath) solution of CrO$_3$ (27.8 g, 278 mmol) in water (53 mL) was added H$_2$SO$_4$ (conc., 23.5 mL). The mixture was cautiously (ice-bath) added to acetone (500 mL). To the resultant mixture was added, dropwise over 2 h, a solution of O—CHF$_2$—O'-3-hydroxy-n-propyl-catechol (16.0 g, 73 mmol, from step (ii) above) in acetone (350 mL), whereafter the reaction mixture was stirred at room temperature overnight. The precipitate was removed by filtration and the filter cake washed with c:acetone. The filtrate was concentrated in vacuo, the residue was dissolved in methylene chloride, and washed with water (3x). The filter-cake was dissolved in the combined water solutions, and the resultant solution was extracted with methylene chloride (2x). The combined methylene chloride phases were dried (Na$_2$SO$_4$) and concentrated in vacuo to afford 15.2 g (89%) of the sub-title compound.

$^1$H-NMR (400 MHz; CDCl$_3$): δ9.64 (s, 1H); 7.12–7.20 (m, 2 H); 6.91–7.02 (m, 2H) 6.30–6.70 (t, 1H); 4.29 (t, 2H); 2.88 (t, 2H)

(iv) 8-Difluoromethoxychroman-4-one

To a cold (ice-bath) solution of 3-(2-OCHF$_2$-phenoxy) propionic acid (12.5 g, 53.8 mmol, from step (iii) above) in methylene chloride (175 mL) under N$_2$ was added, dropwise, boron trifluoride dimethyl etherate (12.5 mL, 136 mmol) and then trifluoroacetic anhydride (20.0 mL, 143.8 mmol). The reaction mixture was stirred at 5° C. for 1 h. The mixture was cooled and water (175 mL) was added cautiously. The organic layer was separated, washed with NaHCO$_3$/aq, dried (Na$_2$SO$_4$) and evaporated. The crude product was chromatographed on silica gel, eluting with methylene chloride, to afford 6.3 g (55%) of the sub-title compound.

$^1$H-NMR (400 MHz; CDCl$_3$): δ7.70–7.74 (dd, 1H); 7.32–7.37 (dd, 1H); 6.93–7.00 (t, 1H); 6.41–6.81 (t, 1H); 4.58–4.64 (t, 2H); 2.80–2.85 (t, 2H)

(v) 6-Chloro-8-difluoromethoxychroman-4-one

To a solution of calcium hypochlorite (29.4 g, 137.8 mmol) in water:acetic acid (125:9.5) was added a solution of 8-difluoromethoxychroman-4-one (7.4 g, 34.6 mmol, see step (iv) above) in acetonitrile (20 mL), whereafter the reaction mixture was stirred overnight. The mixture was diluted with water and extracted with ether (3x) and with EtOAc (1x). The combined organic layers were washed with water (3x), dried (Na$_2$SO$_4$) and evaporated, yielding 8.0 g (93%) of the subtitle compound.

$^1$H-NMR (400 MHz; CDCl$_3$): δ7.70–7.73 (d, 1H); 7.33–7.37 (d, 1H); 6.40–6.80 (t, 1H); 4.63 (t, 2H); 2.86 (t, 2H)

(vi) 4-Methylene-6-chloro-8-difluoromethoxychromane

To a solution of dimethyl methylphosphonate (8.9 g, 71.1 mmol) in dry THF (55 mL) under N$_2$ was added, dropwise over 1 h at −70° C., n-butyllithium in hexane (1.6M, 49.2 mL). The mixture was stirred for 30 minutes at −70° C., whereafter a solution of 6-chloro-8-difluoromethoxychroman-4-one (6.8 g, 27.35 mmol, from step (v) above) in dry THF (15 mL) was added, dropwise over 30 minutes at −70° C. The reaction mixture was stirred for 2 h at −70° C., whereafter NH$_4$Cl (aq., sat., 110 mL) was added, and then water (50 mL). The layers were separated and the aqueous phase was extracted with EtOAc. The combined organic layers were washed with brine, dried (Na$_2$SO$_4$) and concentrated. The residue was dissolved in DMF (85 mL). To the solution was added anhydrous potassium carbonate (27.4 g, 201.0 mmol) and water (3.6 ml). The mixture was warmed for 2 h at 120° C. (oil-bath). After the mixture had reached room temperature water (80 mL) was added. The mixture was extracted with EtOAc. The combined organic layers were washed with citric acid (aq., 10%) and with brine, dried (Na$_2$SO$_4$) and evaporated. The crude product was chromatographed on silica gel, eluting with heptane:methylene chloride (8:2), to afford 3.2 g (47%) of the sub-title compound.

$^1$H-NMR (400 MHz; CDCl$_3$): δ7.38 (d, 1H); 7.03 (d, 1H); 6.33–6.74 (t, 1H); 6.52 (s, 1H); 4.99 (s, 1H); 4.27 (t, 2H); 2.66 (t, 2H)

(vii) (S)- or (R)-4-Hydroxy-4-hydroxymethyl-6-chloro-8-difluoromethoxychromane To a mixture of tert-butanol (46 mL) and water (46 mL) was added AD-mix-β (18.6 g). The mixture was cooled to 0° C. 4-Methylene-6-chloro-8-difluoromethoxychromane (3.2 g 12.97 mmol, see step (vi) above) in tert-butanol (11 mL) and water (11 mL) was added. The mixture was stirred at 0° C. for 24 h. Sodium sulfite (19.0 g, 150.74 mmol) was added, and the mixture was allowed to warm to room temperature and stirred for 1 h. The layers were separated and the aqueous phase was extracted with EtOAc (2x). The combined ethyl acetate phases were dried (Na$_2$SO$_4$) and evaporated. The crude product was chromatographed on silica gel, eluting with methylene chloride:ethyl acetate (4:6), to afford 3.2 g (88%) of the sub-title compound.

$^1$H-NMR (400 MHz; CD$_3$OD): δ7.38 (d, 1H); 7.07 (d, 1H); 6.51–6.74 (t, 1H); 4.86 (s, 2H); 4.3 (m, 2H); 3.70 (dd, 2H); 2.25–2.35 (m, 1H); 1.91–2.02 (m, 1H)

(viii) (S)- or (R)-4-Hydroxy-6-chloro-8-difluoromethoxychroman-4-yl carboxylic acid To a solution of (S)- or (R)-4-hydroxy-4-hydroxymethyl-6-chloro-8-difluoromethoxychromane (3.2 g, 11.4 mmol, from step (vii) above) in acetone (25 mL) was added non-ionized water (110 mL), then sodium hydrogencarbonate (2.13 g, 22.2 mmol) and Pt/C 5%, 58% water (2.13 g). A stream of air was bubbled through the solution with stirring at 75° C. (oil-bath) overnight. The solution was filtered through Celite and the filter-cake was washed with water. The acetone-water solution was acidified (HCl, 2M) to pH 2, saturated with NaCl and extracted with EtOAc (3x). The combined ethyl acetate phases were washed with water (2x) and with brine, then dried (Na$_2$SO$_4$) and concentrated. The residue was dissolved in ether. The ether solution was washed with water (3x) and concentrated, yielding 2.4 g (71%) of the sub-title compound.

$^1$H-NMR (400 MHz; CD$_3$OD): δ7.19 (d, 1H); 7.11 (d, 1H); 6.54–6.75 (t, 1H); 4.90–5.30 (s, 2H); 4.43–4.52 (m, 1H); 4.22–4.32 (dt, 1H); 2.44–2.55 (dt, 1H); 2.06–2.16 (dd, 1H) [α]$_D^{20}$=−20° C. (c=1%, MeOH)

(ix) (S)- or (R)-4-Hydroxy-6-chloro-8-difluoromethoxychroman-4-yl-C(O)-Aze-Pab(Teoc)

To ethyl acetate (20 mL) saturated with HCl was added Boc-Aze-Pab(Teoc) (0.33 g, 0.66 mmol, see Example 4(iii) above). The mixture was kept at room temperature for 15 minutes, whereafter it was concentrated. To the residue dissolved in DMF (4.5 mL) was added (S)- or (R)-4-hydroxy-6-chloro-8-difluoromethoxychroman-4-yl carboxylic acid (0.195 g, 0.66 mmol, from step (viii) above), then PyBOP (0.36 g, 0.68 mmol) and DIPEA (0.33 g, 0.68 mmol). The mixture was stirred at room temperature for 2 h, diluted with water (175 mL) and sodium hydrogencarbonate was added to give a pH of 9. The mixture was then extracted with EtOAc (3×). The combined ethyl acetate phases were washed with water and with brine, and then dried ($Na_2SO_4$) and concentrated. The crude product was further purified using preparative HPLC ($CH_3CN$:0.1 M ammonium acetate, 60:40). The fractions of interest were concentrated. The residue was dissolved in water. The aqueous phase was extracted with EtOAc (3×). The combined ethyl acetate phases were washed with water and with brine, and then dried ($Na_2SO_4$) and concentrated, yielding 0.3 g (68%) of the sub-title compound.

$^1$H-NMR (400 MHz; $CD_3OD$): δ7.80 (m, 2H); 7.09–7.44 (m, 3H); 6.52–7.00 (dt, 1H); 5.48 (m, 1H); 4.86 (s, 4H); 3.80–4.60 (m, 8H)); 1.80–2.80 (m, 4H); 1.22 (t, 1H); 1.08 (t, 2H); 0.07 (s, 9H).

(x) (S)- or (R)-4-Hydroxy-6-chloro-8-difluoromethoxychroman-4-yl-C(O)-Aze-Pab x HOAc To a cold solution of (S)- or (R)-4-hydroxy-6-chloro-8-difluoromethoxychroman-4-yl-C(O)-Aze-Pab(Teoc) (0.30 g, 0.459 mmol, from step (ix) above) in methylene chloride (1 mL) was added TFA (10 mL). The mixture was stirred for 1 h, and then concentrated carefully in vacuo. The crude product was further purified using preparative HPLC ($CH_3CN$:0.1 M ammonium acetate, 30:70). The fractions of interest were concentrated. The product was dissolved in a minimal amount of $CH_3CN$/water and freeze dried (2×), yielding 0.24 g (92%) of the title compound.

$^1$H-NMR (400 MHz; $CD_3OD$): δ7.68–7.78 (dd, 2H); 7.49–7.57 (dd, 2H); 7.27 (d, 1H); 7.09–7.15 (dd, 1H); 6.56–6.94 (t, 1H); 5.51–5.54 (m, 1H); 4.90–5.02 (m, 8H); 3.98–4.62 (m, 6H); 2.08–2.80 (m, 5H); 1.91 (s, 3H).

$^{13}$C NMR (400 MHz; $CD_3OD$): carbonyl and/or amidine carbons 179.30; 175.93; 175.37; 174.31; 173.04; 168.11.

MS (m/z) 509 (M+1)$^+$

Example 9

(S)- or (R)-4-Hydroxy-6-chloro-8-difluoromethoxychroman-4-yl-C(O)-Aze-Pab(OMe)

To a solution of (S)- or (R)-4-hydroxy-6-chloro-8-difluoromethoxychroman-4-yl carboxylic acid (0.065 g, 0.22 mmol, see Example 8(viii) above) in DMF (1.5 mL) was added H-Aze-Pab(OMe) x 2HCl (0.060 g, 0.23 mmol, see international patent application WO 98/57932), then PyBOP (0.12 g, 0.23 mmol) and DIPEA (0.11 g, 0.85 mmol). The mixture was stirred at room temperature for 1.5 h and then evaporated. The residue was dissolved in water (50 mL) and sodium hydrogencarbonate was added to give a pH of 9. The mixture was extracted with EtOAc (3×). The combined ethyl acetate phases were washed with $NaHCO_3$/aq (2×) and with water, dried ($Na_2SO_4$) and concentrated. The crude product was further purified using preparative HPLC ($CH_3CN$:0.1 M ammonium acetate, 50:50). The fractions of interest were concentrated. The product was dissolved in a minimal amount of $CH_3CN$/water and freeze dried (2×), yielding 0.080 g (67%) of the title compound.

$^1$H-NMR (400 MHz; $CD_3OD$): δ7.44 (d, 1H); 7.10–7.26 (m, 2H); 6.91–7.01 (d, 1H); 6.40–6.80 (t, 1H); 5.31 (m, 1H); 4.67 (s, 2H); 4.20–4.40 (m, 2H); 3.80–4.15 (m, 2H); 3.66 (s, 1H); 2.97–3.01 (m, 4H); 2.50–2.64 (m, 1H); 1.87–2.41 (m, 4H); 1.67–1.71 (t, 3H)

$^{13}$C NMR (400 MHz; $CD_3OD$): carbonyl and/or amidine carbons 175.87; 175.31; 174.04; 172.73

MS (m/z) 539 (M+1)$^+$

Example 10

The title compounds of Examples 6 and 8 were tested in Test A above and were found to exhibit an $IC_{50}TT$ value of less than 0.1 μM.

Example 11

The title compounds of Examples 1 to 5, 7 and 9 were tested in Test E above and were all found to exhibit oral and/or parenteral bioavailability in the rat as the corresponding active inhibitor (free amidine).

Example 12

The title compounds of Examples 1 to 5 were tested in Test G above and all exhibited formation of the corresponding active inhibitor (free amidine).

Abbreviations

Ac=acetyl
AcOH=acetic acid
Aze=azetidine-2-carboxylate
AzeOH=azetidine-2-carboxylic acid
Bzl=benzyl
DIPEA=diisopropylethylamine
DMAP=4-(N,N-dimethyl amino)pyridine
DMF=dimethylformamide
DMSO=dimethylsulphoxide
EDC=1-(3-dimethylaminopropyl)-3-ethylcarbodiimide hydrochloride
Et=ethyl
ether=diethyl ether
EtOAc=ethyl acetate
EtOH=ethanol
h=hours
HATU=O-(azabenzotriazol-1-yl)-N,N,N',N'-tetramethyluronium hexafluorophosphate
HBTU=[N,N,N',N'-tetramethyl-O-(benzotriazol-1-yl) uronium hexafluorophosphate]
HCl(g)=hydrogen chloride gas
HOAc=acetic acid
LC=liquid chromatography
Me=methyl
MeOH=methanol
Pab=para-amidinobenzylamino
H-Pab para-amidinobenzylamine
PyBOP=(benzotriazole-1-yl-oxy) tripyrrolidinophosphonium hexafluorophosphate
RPLC=reverse phase high performance liquid chromatography
RT=room temperature
TBTU=[N,N,N',N'-tetramethyl-O-(benzotriazol-1-yl) uronium tetrafluoroborate]
TEA=triethylamine
Teoc=2-(trimethylsilyl)ethoxycarbonyl
THF=tetrahydrofuran
TLC=thin layer chromatography
Val=L-valine
Z=benzyloxycarbonyl Prefixes n, s, i and t have their usual meanings: normal, secondary, iso and tertiary.

What is claimed is:
1. A compound of formula I,

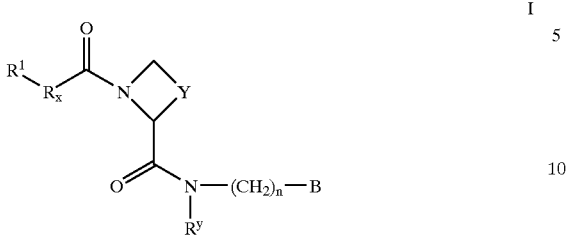

I wherein
- $R^1$ represents H, $C_{1-4}$ alkyl (optionally substituted by one or more substituents selected from cyano, halo, OH, $C(O)OR^{1a}$ or $C(O)N(R^{1b})R^{1c}$) or $OR^{1d}$;
- $R^{1d}$ represents H, $C(O)R^{11}$, $SiR^{12}R^{13}R^{14}$ or $C_{1-6}$ alkyl, which latter group is optionally substituted or terminated by one or more substituent selected from $OR^{15}$ or $(CH_2)_q R^{16}$;
- $R^{12}$, $R^{13}$ and $R^{14}$ independently represent H, phenyl or $C_{1-6}$ alkyl;
- $R^{16}$ represents $C_{1-4}$ alkyl, phenyl, OH, $C(O)OR^{17}$ or $C(O)N(H)R^{18}$;
- $R^{18}$ represents H, $C_{1-4}$ alkyl or $CH_2C(O)OR^{19}$;
- $R^{15}$ and $R^{17}$ independently represent H, $C_{1-6}$ alkyl or $C_{1-3}$ alkylphenyl;
- $R^{1a}$, $R^{1b}$, $R^{1c}$, $R^{11}$ and $R^{19}$ independently represent H or $C_{1-4}$ alkyl; and
- q represents 0, 1 or 2;
- $R_x$ represents a structural fragment of formula IIa,

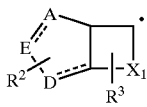

IIa wherein
- the dotted lines independently represent optional bonds;
- A and E independently represent CH;
- D represents $-CH=CH-$;
- $X_1$ represents $O-A^3$;
- $A^3$ represents $C_{1-3}$ alkylene;
- $R^2$ represents one or more optional substituents selected from $C_{1-4}$ alkyl, $C_{1-4}$ alkoxy (which latter two groups are optionally substituted by one or more halo substituent), methylenedioxy, halo, hydroxy, cyano, nitro, $S(O)_2NH_2$, $C(O)OR^{26}$, $SR^{26}$, $S(O)R^{26a}$, $S(O)_2R^{26a}$ or $N(R^{27})R^{28}$;
- $R^3$ represents one or more optional substituents selected from OH, $C_{1-4}$ alkoxy, $C_{1-6}$ alkyl (optionally substituted by one or more halo group), or $N(R^{29a})R^{29b}$;
- $R^{29a}$ and $R^{29b}$ independently represent H, $C_{1-4}$ alkyl or $C(O)R^{30}$;
- $R^{26}$ represents H or $C_{1-4}$ alkyl;
- $R^{26a}$ represents $C_{1-4}$ alkyl;
- $R^{27}$ and $R^{28}$ independently represent H, $C_{1-4}$ alkyl or $C(O)R^{30}$, or together represent $C_{3-6}$ alkylene, thus forming a 4- to 7-membered ring, which ring is optionally substituted, on a carbon atom that is α to the nitrogen atom, with an $=O$ group;
- $R^{30}$ represents, at each occurrence, H or $C_{1-4}$ alkyl;
- Y independently represents $CH_2$, $(CH_2)_2$ or $CH=CH$;
- $R^y$ represents H or $C_{1-4}$ alkyl;
- n represents 0, 1, 2, 3 or 4; and
- B represents a structural fragment of formula IIIa or IIIc

IIIa

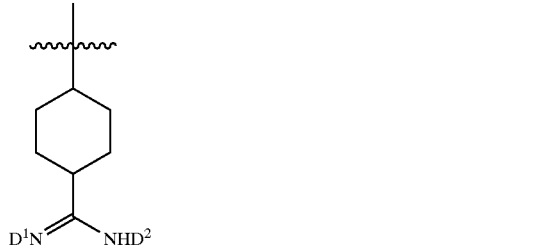

IIIc wherein
- $X^5$, $X^6$, $X^7$ and $X^8$ independently represent CH;
- $R^{31}$ represents an optional substituent selected from halo, $C_{1-4}$ alkyl (which group is optionally substituted by one or more halo group), $N(R^{32})R^{33}$, $OR^{34}$ or $SR^{35}$;
- $R^{32}$ and $R^{33}$ independently represent H, $C_{1-4}$ alkyl or $C(O)R^{36}$;
- $R^{34}$, $R^{35}$ and $R^{36}$ independently represent H or $C_{1-4}$ alkyl; and
- one of $D^1$ and $D^2$ represents H, and the other represents H, $OR^a$, $NHR^a$, $C(=X^{11})X^{12}R^b$, or $D^1$ and $D^2$ together represent a structural fragment of formula IVa:

IVa

- $R^a$ represents H or $-A^5[X^{14}]_n[C(O)]_r R^e$;
- $R^b$ represents $-A^5[X^{14}]_n[C(O)]_r R^e$;
- $A^5$ represents, at each occurrence, a single bond or $C_{1-12}$ alkylene (which alkylene group is optionally interrupted by one or more O, $S(O)_m$ and/or $N(R^f)$ group, and is optionally substituted by one or more of halo, OH, $N(H)C(O)R^g$, $C(O)N(R^g)R^h$, $C_{3-7}$-cycloalkyl (which cycloalkyl group is optionally interrupted by one or more O, $S(O)_m$ and/or $N(R^f)$ group and/or is optionally substituted by one or more substituents selected from $C_{1-6}$ alkyl, $C_{1-6}$ alkoxy, halo, $=O$ or $=S$), Het and $C_{6-10}$ aryl (which aryl and Het groups are themselves optionally substituted by one or more substituents selected from $C_{1-6}$ alkyl (optionally substituted by one or more halo substituent), $C_{1-6}$ alkoxy, halo, cyano, $C(O)OR^g$, $C(O)N(R^g)R^h$ and $N(R^f)R^g$));

$R^c$ and $R^d$ both represent H; or one of $R^c$ and $R^d$ represents H or $C_{1-7}$ alkoxy and the other represents $C_{1-7}$ alkyl (which alkyl group is optionally interrupted by one or more O atoms); or $R^c$ and $R^d$ together represent $C_{3-8}$ cycloalkyl, which cycloalkyl group is interrupted by one or more O, $S(O)_m$ and/or $N(R^f)$ group;

$R^e$ represents, at each occurrence, H, $C_{1-12}$ alkyl (which alkyl group is optionally interrupted by one or more O, $S(O)_m$ and/or $N(R^f)$ group, and/or is optionally substituted by one or more substituents selected from halo, OH, $N(H)C(O)R^g$ and $C(O)N(R^g)R^h$), $A^7$—$C_{3-7}$-cycloalkyl (which cycloalkyl group is optionally interrupted by one or more O, $S(O)_m$ and/or $N(R^f)$ group and/or is substituted by one or more substituents selected from $C_{1-6}$ alkyl, $C_{1-6}$ alkoxy, halo, =O and =S), $A^7$—$C_{6-10}$ aryl or $A^7$-Het (which aryl and Het groups are optionally substituted by one or more substituents selected from $C_{1-6}$ alkyl (optionally substituted by one or more halo substituent), $C_{1-6}$ alkoxy, halo, cyano, $C(O)OR^g$, $C(O)N(R^g)R^h$ and $N(R^f)R^g$);

$A^7$ represents a single bond or $C_{1-7}$ alkylene (which alkylene group is optionally interrupted by one or more O, $S(O)_m$ and/or $N(R^f)$ group, and/or are optionally substituted by one or more of halo, OH, $N(H)COR^g$ and $CON(R^g)R^h$);

Het represents, at each occurrence, a five- to ten-membered heteroaryl group, which may be aromatic in character, containing one or more nitrogen, oxygen or sulphur atoms in the ring system;

n and r independently represent 0 or 1;

$X^{11}$, $X^{12}$ and $X^{14}$ independently represent O or S;

$X^{13}$ represents O or $N(R^f)$;

$R^f$ represents, at each occurrence, H, $C_{1-4}$ alkyl or $C(O)R^g$;

$R^g$ and $R^h$ independently represent, at each occurrence, H or $C_{1-4}$ alkyl; and m represents, at each occurrence, 0, 1 or 2;

or a pharmaceutically acceptable salt thereof; provided that:

when $A^5$ represents a single bond, then n and r both represent 0;

when $A^5$ represents $C_{12}$ alkylene, then n represents 1;

when $A^5$ represents —$CH_2$—, n is 1 and r is 0, then $R^e$ does not represent H; and the compound is not:

(S)- or (R)-1-hydroxy-7-methoxytetralin-1-yl
(R)- or (S)-1-hydroxy-7-methoxytetralin-1-yl
(S)- or (R)-1-hydroxy-7-methoxytetralin-1-yl
(R)- or (S)-1-hydroxy-7-methoxytetralin-1-yl
1-hydroxy-5-methoxytetralin-1-yl
1-hydroxy-5,7-dimethyltetralin-1-yl
1-hydroxy-7-aminotetralin-1-yl
1-hydroxytetralin-1-yl
7-methoxytetralin-1-yl;
(R)- or (S)-7-methoxy-1-methyltetralin-1-yl;
4-hydroxy-6-methoxychroman-4-yl;
(S)- or (R)-1-hydroxy-4-methoxyindan-1-yl;
1-hydroxy-5-methoxytetralin-1-yl
(S)- or (R)-1-hydroxy-7-methoxytetralin-1-yl
4-hydroxy-6-methoxychroman-4-yl-C(O)-Aze-Pab(OH);
4-hydroxy-6-methoxychroman-4-yl-C(O)-Aze-Pab(OMe);
(S)- or (R)-1-hydroxy-7-methoxytetralin-1-yl-C(O)-Aze-Pab-;
(S)- or (R)-1-hydroxy-7-methoxytetralin-1-yl;
7-methoxy-1-allyltetralin-1-yl-C(O)-Aze-Pab x HOAc;
(S)- or (R)-1-hydroxy-7-chlorotetralin-1-yl-C(O)-Pro-Pab;
1-n-propyl-7-methoxytetralin-1-yl-C(O)-Aze-Pab x HOAc;
6-chloro-4-hydroxychroman-4-yl-C(O)-Aze-Pab x HOAc;
4-hydroxychroman-4-yl-C(O)-Aze-Pab x HOAc;
6,8-dichloro-4-hydroxychroman-4-yl-C(O)-Aze-Pab x HOAC;
6-fluoro-4-hydroxychroman-4-yl-C(O)-Aze-Pab x HOAc;
4-hydroxy-6-methylchroman-4-yl-C(O)-Aze-Pab x HOAc;
8-chloro-4-hydroxy-6-methoxychroman-4-yl-C(O)-Aze-Pab x HOAc;
6-chloro-4-hydroxy-8-methylchroman-4-yl-C(O)-Aze-Pab x HOAc;
(S)- or (R)-1-hydroxy-7-methoxytetralin-1-yl-C(O)-Aze-Pab(O—C(O)-i-Pr);
(S)- or (R)-1-hydroxy-7-methoxytetralin-1-yl-C(O)-Aze-Pab(O—C(O)-Et);
(S)- or (R)-1-hydroxy-7-methoxytetralin-1-yl-C(O)-Aze-Pab(O—C(O)-Ch);
(S)- or (R)-1-hydroxy-7-methoxytetralin-1-yl-C(O)-Aze-Pab(O-allyl);
(S)- or (R)-1-hydroxy-7-methoxytetralin-1-yl-C(O)-Aze-Pab(O-Bzl);
(S)- or (R)-1-hydroxy-7-methoxytetralin-1-yl-C(O)-Aze-Pab-(CO—O-methallyl);
1-hydroxy-7-aminotetralin-1-yl-C(O)-Aze-Pab(OH);
(S)- or (R)-1-hydroxy-7-methoxytetralin-1-yl-C(O)-Aze-Pab(O-Val);
(S)- or (R)-1-hydroxy-7-methoxytetralin-1-yl-C(O)-Aze-(Me)Pab; or
9-hydroxyfluoren-9-yl-C(O)-Aze-Pab x HOAc.

2. A compound as claimed in claim 1 wherein $R^1$ represents OH or $C_{1-4}$ alkyl (which latter group is optionally substituted by cyano or OH).

3. A compound as claimed in claim 1 wherein the dotted lines represent bonds.

4. A compound as claimed in claim 1 wherein $A^3$ represents $C_1$- or $C_2$-alkylene.

5. A compound as claimed in claim 1 wherein Y represents $CH_2$ or $(CH_2)_2$.

6. A compound as claimed in claim 1 wherein B represents a structural fragment of formula IIIa in which $X^5$, $X^6$, $X^7$ and $X_8$ all represent CH.

7. A compound as claimed in claim 1 wherein, when $D^1$ and $D^2$ together represent a structural fragment of formula IVa, in which $X^{13}$ is O, then one of $R^c$ and $R^d$ represents H or $C_{17}$ alkoxy and the other represents $C_{1-7}$ alkyl.

8. A compound as claimed in claim 1, wherein, when $D^1$ or $D^2$ represents $OR^a$ and $R^a$ represents —$A^5[X^{14}]_n[C(O)]_rR^e$, and (i) $A^5$ is a single bond, then $R^e$ is:
(1) $A^7$-aryl, optionally substituted by one or more halo, $C_{1-6}$ alkoxy, $C_{1-6}$ alkyl or halo-$C_{1-6}$-alkyl substituents; or
(2) H or linear, branched, optionally unsaturated, and/or cyclic, $C_{1-2}$ alkyl, which cyclic alkyl group is optionally interrupted by an O atom and, optionally, a further O atom or $S(O)_m$ group; or when (ii) $A^5$ is linear or branched $C_{1-12}$ alkylene, $X^{14}$ is O and r is 0, then $R^e$ is $C_{1-3}$ alkyl or $A^7$-aryl, in which $A^7$ is a single bond.

9. A compound as claimed in claim 1, wherein, when $D^1$ or $D^2$ represents $OR^a$, then $R^a$ is H or $C_{1-4}$ alkyl.

10. A compound as claimed in claim 1, wherein, when $D^1$ or $D^2$ represents —C(=$X^{11}$)$X^{12}R^b$, in which $X^{11}$ represents O and $X^{12}$ represents O or S, and, in which $R^b$ group, $A^5$ represents a single bond then $R^e$ represents optionally unsaturated $C_{1-6}$ alkyl, $A^7$—$C_{6-10}$-aryl (in which $A^7$ represents a single bond or $C_{1-2}$ alkylene, and which $A^7$—$C_{6-10}$-aryl group is optionally substituted by one or more halo, $C_{1-4}$ alkyl and/or $C_{1-4}$ alkoxy groups), or $A^7$—$C_{3-7}$-cycloalkyl, in which $A^7$ represents a single bond or linear or branched $C_{1-7}$ alkylene, and which cycloalkyl group is optionally substituted by $C_{1-3}$alkyl.

11. A compound of formula I, as defined in claim 1, wherein the fragment

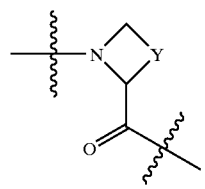

is in the S-configuration.

12. A pharmaceutical formulation including a compound as defined in claim 1, or a pharmaceutically acceptable salt thereof, in admixture with a pharmaceutically acceptable adjuvant, diluent or carrier.

13. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition and wherein the condition is selected from: thrombosis; hypercoagulability in blood and tissues; inherited or acquired activated protein C resistance; inherited or acquired deficiencies in antithrombin III, protein C, protein S or heparin cofactor II; circulating antiphospholipid antibodies; homocysteinemi; heparin induced thrombocytopenia; defects in fibrinolysis; Alzheimer's disease; venous thrombosis; pulmonary embolism; arterial thrombosis; disseminated intravascular coagulation caused by bacteria, multiple trauma or intoxication; idiopathic and adult respiratory distress syndrome; pulmonary fibrosis following treatment with radiation or chemotherapy; septic shock; septicemia; inflammatory responses; edema; acute or chronic atherosclerosis; coronary arterial disease; cerebral arterial disease; peripheral arterial disease; reperfusion damage; restenosis after precutaneous trans-luminal angioplastry; and pancreatitis.

14. A process for the preparation of compounds of formula I which comprises:

(i) the coupling of a compound of formula IV,

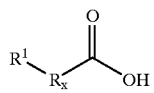

IV wherein $R^1$ and $R_x$ are as defined in claim 1 with a compound of formula V,

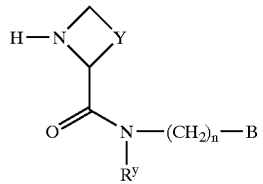

V wherein $R^y$, Y, n and B are as defined in claim 1;

(ii) the coupling of a compound of formula VI,

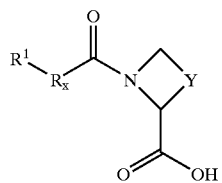

VI wherein $R^1$, $R_x$ and Y are as defined in claim 1 with a compound of formula VII,

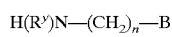

H($R^y$)N—(CH$_2$)$_n$—B    VII wherein $R^y$, n and B are as defined in claim 1;

(iii) for compounds of formula I in which $D^1$ or $D^2$ represents $OR^a$ or $NHR^a$, reaction of a compound of formula VIII,

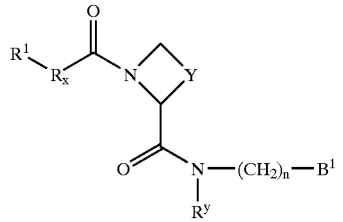

VIII wherein $B^1$ represents a structural fragment of formula IIId, or IIIf

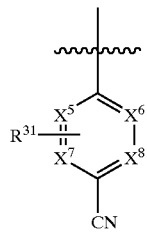

IIId

-continued

IIIf

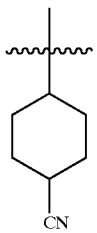

and $R^1$, $R_x$, Y, $R^y$, n, $R^{31}$, $X^5$, $X^6$, $X^7$ and $X^8$ are as defined in claim 1 with a compound of formula IX, $$H_2NX^aR^a \qquad IX$$

wherein $X^a$ represents O or NH and $R^a$ is as defined in claim 1;

(iv) for compounds of formula I in which $D^1$ or $D^2$ represents $OR^a$ or $NHR^a$, reaction of a compound of formula I in which $D^1$ or $D^2$ (as appropriate) represents $C(O)OR^{b1}$, in which $R^{b1}$ represents a protecting group with a compound of formula IX as defined above;

(v) for compounds of formula I in which $D^1$ or $D^2$ represents $OR^a$ or $NHR^a$, $R^a$ represents $-A^5[X^{14}]_n[C(O)]_rR^e$, in which $A^5$ does not represent a single bond, and n represent 1, reaction of a compound of formula I in which $D^1$ or $D^2$ (as appropriate) represents OH or $NH_2$, with a compound of formula X, $$L^1A^{5a}[X^{14}][C(O)]_rR^e \qquad X$$

wherein $L^1$ represents a suitable leaving group, $A^{5a}$ represents $A^5$, as defined in claim 1 except that it does not represent a single bond, and $X^{14}$, r and $R^e$ are as defined in claim 1;

(vi) for compounds of formula I in which $D^1$ or D2 represents $OR^a$ or $NHR^a$, $R^a$ represents $-A^5[X^{14}]_n[C(O)]_rR^e$, in which $A^5$ represents $C_{2-12}$ alkylene, which alkylene group is branched at the carbon atom that is α to the O or N atom of $OR^a$ or $NHR^a$ (as appropriate), and which group is optionally branched at the carbon atom that is β to that atom, n represents 1, r represents 0 and $R^e$ is as defined in claim 1, reaction of a compound of formula I in which $D^1$ or $D^2$ (as appropriate) represents OH or $NH_2$, with a compound of formula XI,

XI

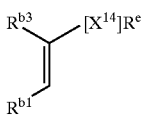

or a geometrical isomer thereof, or a mixture of such geometrical isomers, in which $R^{b1}$ and $R^{b3}$ each represent H or an alkyl group, provided that the total number of carbon atoms provided by $R^{b1}$ and $R^{b3}$ does not exceed 10, and wherein $X^{14}$ and $R^e$ are as defined in claim 1;

(vii) for compounds of formula I in which $D^1$ or D2 represents $OR^a$ or $NHR^a$, $R^a$ represents $-A^5[X^{14}]_n[C(O)]_rR^e$, in which $A^5$ represents a single bond, and $R^e$ represents $A^7-C_{3-6}$-cycloalkyl, in which $A^7$ represents a single bond, and the cycloalkyl group is interrupted by at least one O or S atom, which atom is between the carbon atom at the point of attachment to the O or NH group of $OR^a$ or $NHR^a$, and a carbon atom that is α to that point of attachment, and which cycloalkyl group is optionally interrupted by one or more O or $S(O)_m$ group and/or optionally substituted by one or more =O group, reaction of a compound of formula I, in which $D^1$ or $D^2$ (as appropriate) represents OH or $NH_2$, with a compound of formula XII,

XII

wherein $X^{15}$ represents O or S and $X^{16}$ represents $C_{1-4}$ alkylene (which alkylene group is optionally interrupted by one or more O or $S(O)_m$ group and/or optionally substituted by one or more =O group);

(viii) for compounds of formula I in which $D^1$ or $D^2$ represents $C(X^{11})X^{12}R^b$, reaction of a compound of formula I in which $D^1$ and $D^2$ both represent H with a compound of formula XIII, $$L^2-C(X^{11})X^{12}R^b \qquad XIII$$

wherein $L^2$ represents a suitable leaving group, and $X^{11}$, $X^{12}$ and $R^b$ are as defined in claim 1;

(ix) for compounds of formula I in which $D^1$ and $D^2$ together represent a structural fragment of formula IVa, reaction of a corresponding compound of formula I in which $D^1$ or $D^2$ represents OH or $NHR^f$ (in which $R^f$ is as defined in claim 1), with a compound of formula XV, $$(R^c)(R^d)C(R^{c1})(R^{c2}) \qquad XV$$

wherein $R^{c1}$ and $R^{c2}$ both represent $-OR^{c3}$, in which $R^{c3}$ represents $C_{1-3}$ alkyl, or together represent =O, and $R^c$ and $R^d$ are as defined in claim 1;

(x) for compounds of formula I in which one or more of $X^5$, $X^6$, $X^7$ and $X^8$ represent N—O, oxidation of a corresponding compound of formula I in which $X^5$, $X^6$, $X^7$ and/or $X^8$ (as appropriate) represent(s) N; or (xi) for compounds of formula I in which any one of Z, $X_1$, $R^2$, $R^4$, $A^5$, $A^7$, $R^c$, $R^d$ and/or $R^e$ comprises or includes a S(O) or a $S(O)_2$ group, oxidation of a corresponding compound of formula I (or a compound corresponding to a compound of formula I) wherein Z, $X_1$, $R^2$, $R^4$, $A^5$, $A^7$, $R^c$, $R^d$ and/or $R^e$ (as appropriate) comprise(s) or include(s) a S group;

(xii) for compounds of formula I in which $D^1$ and $D^2$ both represent H, removal of a $OR^a$, $NHR^a$ or $C(=X^{11})X^{12}R^b$ group (in which $R^a$, $R^b$, $X^{11}$ and $X^{12}$ are as defined in claim 1), or removal of a structural fragment of formula IVa as defined in claim 1, from a corresponding compound of formula I; or (xiii) introduction and/or interconversion of a substituent on an aromatic and/or non-aromatic, carbocyclic and/or heterocyclic ring in a corresponding compound of formula I.

* * * * *

UNITED STATES PATENT AND TRADEMARK OFFICE
CERTIFICATE OF CORRECTION

PATENT NO. : 6,750,243 B1
DATED : June 15, 2004
INVENTOR(S) : Inghardt et al.

It is certified that error appears in the above-identified patent and that said Letters Patent is hereby corrected as shown below:

Title page,
Item [73], Assignee, please delete "Sodertalje" and insert -- Södertälje --.

Column 2,
Line 21, please delete "land" and insert -- and --.
Line 64, please delete "$C_{1-6}$alkyl" and insert -- $C_{1-6}$ alkyl --.

Column 5,
Line 53, please delete "C(O N($R^g$)$R^h$" and insert -- C(O)N($R^g$)$R^h$ --.
Line 58, please delete "are" and insert -- is --.

Column 6,
Line 39, please delete ";," and insert -- ; --.
Line 48, please delete "C(O)OCH$_2$CH1$_3$)" and insert -- (C(O)OCH$_2$CCl$_3$) --.
Line 67, please delete "(Q-C(O)-Et)" and insert -- (O-C(O)-Et) --.

Column 9,
Line 64, please delete "2and" and insert -- 2 and --.

Column 11,
Line 25, please delete "$C_{1-4}$," and insert -- $C_{1-4}$ --.

Column 14,
Lines 4 and 30, please delete "define" and insert -- defined --.
Line 36, please delete "cycloallyl" and insert -- cycloalkyl --.

Column 15,
Line 1, please delete "define" and insert -- defined --.

Column 18,
Line 34, please delete "NaOH, For to" and insert -- NaOH. For --.

Column 19,
Line 30, please delete "define" and insert -- defined --.

Column 21,
Line 17, pleae delete "define" and insert -- defined --.

Column 22,
Lines 7 and 40, please delete "define" and insert --defined --.

UNITED STATES PATENT AND TRADEMARK OFFICE
CERTIFICATE OF CORRECTION

PATENT NO. : 6,750,243 B1
DATED : June 15, 2004
INVENTOR(S) : Inghardt et al.

It is certified that error appears in the above-identified patent and that said Letters Patent is hereby corrected as shown below:

Column 23,
Line 13, please delete "define" and insert -- defined --.

Column 24,
Line 3, please delete "H, In" and insert -- H. In --.

Column 27,
Line 25, please delete "NIH U/mL" and insert -- NIHU/mL --.

Column 39,
Line 7, please delete "c:acetone" and insert -- acetone --.

Column 43,
Line 46, please delete "-CH=CH;" and insert -- -CH=CH-; --.

Column 45,
Line 32, please delete "are" and insert -- is --.
Lines 55-56, please delete "(S)- or (R)-1-hydroxy-7-methoxytetralin-1-yl; (R)- or (S)-1-hydroxy-7-methoxytetralin-1-yl;

(S)- or (R)-1-hydroxy-7-methoxytetralin-1-yl;

(R)- or (S)-1-hydroxy-7-methoxytetralin-1-yl;

1-hydroxy-5-methoxytetralin-1-yl;

1-hydroxy-5,7-dimethyltetralin-1-yl;

1-hydroxy-7-aminotetralin-1-yl;

1-hydroxytetralin-1-yl;

7-methoxytetralin-1-yl;

(R)- or (S)-7-methoxy-1-methyltetralin-1-yl;".

Line 66, please delete "4-hydroxy-6-methoxychroman-4-yl" and insert -- 4-hydroxy-6-methoxychroman-4-yl-C(O)-Aze-Pab x OAc; --.

Column 45, line 66 to Column 46, line 2,
Please delete "(S)- or (R)-1-hydroxy-7-methoxyindan-1-yl;

1-hydroxy-5-methoxytetralin-1-yl;

(S)- or (R)-1-hydroxy-7-methoxytetralin-1-yl; --.

UNITED STATES PATENT AND TRADEMARK OFFICE
CERTIFICATE OF CORRECTION

PATENT NO. : 6,750,243 B1
DATED : June 15, 2004
INVENTOR(S) : Inghardt et al.

It is certified that error appears in the above-identified patent and that said Letters Patent is hereby corrected as shown below:

<u>Column 46,</u>
Lines 5-10, please delete "(*S*)- or (*R*)-1-hydroxy-7-methoxytetralin-1-yl;

(*S*)- or (*R*)-1-hydroxy-7-methoxytetralin-1-yl;

7-methoxy-1-allyltetralin-1-yl-C(O)-Aze-Pab x HOAc;

(*S*)- or (*R*)-1-hydroxy-7-chlorotetralin-1-yl-C(O)-Pro-Pab;

1-*n*-propyl-7-methoxytetralin-1-yl-C(O)-Aze=Pab x HOAc; --.
Line 14, please delete "HOAC" and insert -- HOAc --.
Lines 20-37, please delete "(*S*)- or (*R*)-1-hydroxy-7-methoxytetralin-1-yl-C(O)-Aze-Pab (O-C(O)-*i*-Pr);

(*S*)- or (*R*)-1-hydroxy-7-methoxytetralin-1-yl-C(O)-Aze-Pab(O-C(O)-Et);

(*S*)- or (*R*)-1-hydroxy-7-methoxytetralin-1-yl-C(O)-Aze-Pab(O-C(O)-Ch);

(*S*)- or (*R*)-1-hydroxy-7-methoxytetralin-1-yl-C(O)-Aze-Pab(O-allyl);

(*S*)- or (*R*)-1-hydroxy-7-methoxytetralin-1-yl-C(O)-Aze-Pab(O-Bzl);

(*S*)- or (*R*)-1-hydroxy-7-methoxytetralin-1-yl-C(O)-Aze-Pab-(CO-O-methallyl);

1-hydroxy-7-aminotetralin-1-yl-C(O)-Aze-Pab(OH);

(*S*)- or (*R*)-1-hydroxy-7-methoxytetralin-1-yl-C(O)-Aze-Pab(O-Val);

(*S*)- or (*R*)-1-hydroxy-7-methoxytetralin-1-yl-C(O)-Aze-(Me)Pab; or 9-hydroxyfluoren-9-yl-C(O)-Aze-Pab x HOAc.".

Line 53, please delete "$C_{17}$ alkoxy" and insert -- $C_{1-7}$ alkoxy --.
Line 62, please delete "$C_{1-2}$ alkyl" and insert -- $C_{1-12}$ alkyl --.

UNITED STATES PATENT AND TRADEMARK OFFICE
CERTIFICATE OF CORRECTION

PATENT NO. : 6,750,243 B1
DATED : June 15, 2004
INVENTOR(S) : Inghardt et al.

It is certified that error appears in the above-identified patent and that said Letters Patent is hereby corrected as shown below:

Column 49,
Line 28, please delete "represent" and insert -- represents --.
Lines 38 and 63, please delete "D2" and insert -- $D^2$ --.

Signed and Sealed this

Tenth Day of May, 2005

JON W. DUDAS
*Director of the United States Patent and Trademark Office*